US011401241B2

(12) United States Patent
Safo et al.

(10) Patent No.: US 11,401,241 B2
(45) Date of Patent: Aug. 2, 2022

(54) AROMATIC ALDEHYDES WITH SUSTAINED AND ENHANCED IN VITRO AND IN VIVO PHARMACOLOGIC ACTIVITY TO TREAT SICKLE CELL DISEASE

(71) Applicants: VIRGINIA COMMONWEALTH UNIVERSITY, Richmond, VA (US); THE CHILDREN'S HOSPITAL OF PHILADELPHIA, Philadelphia, PA (US)

(72) Inventors: Martin K. Safo, Richmond, VA (US); Yan Zhang, Glen Allen, VA (US); Piyusha Pradeep Pagare, Richmond, VA (US); Guoyan Xu, Henrico, VA (US); Mohini Ghatge, Glen Allen, VA (US); Jurgen Venitz, Richmond, VA (US); Osheiza Abdulmalik, Wynnewood, PA (US)

(73) Assignees: VIRGINIA COMMONWEALTH UNIVERSITY, Richmond, VA (US); THE CHILDREN'S HOSPITAL OF PHILADELPHIA, Philadelphia, PA (US)

(*) Notice: Subject to any disclaimer, the term of this patent is extended or adjusted under 35 U.S.C. 154(b) by 0 days.

(21) Appl. No.: 16/982,745

(22) PCT Filed: Mar. 18, 2019

(86) PCT No.: PCT/US2019/022678
§ 371 (c)(1),
(2) Date: Sep. 21, 2020

(87) PCT Pub. No.: WO2019/182938
PCT Pub. Date: Sep. 26, 2019

(65) Prior Publication Data
US 2021/0002225 A1    Jan. 7, 2021

Related U.S. Application Data

(60) Provisional application No. 62/646,434, filed on Mar. 22, 2018.

(51) Int. Cl.
| | |
|---|---|
| C07D 213/80 | (2006.01) |
| A61P 7/00 | (2006.01) |
| A61K 9/00 | (2006.01) |
| C07D 213/79 | (2006.01) |
| C07D 401/04 | (2006.01) |
| C07D 409/04 | (2006.01) |

(52) U.S. Cl.
CPC .......... C07D 213/80 (2013.01); A61K 9/0053 (2013.01); A61P 7/00 (2018.01); C07D 213/79 (2013.01); C07D 401/04 (2013.01); C07D 409/04 (2013.01)

(58) Field of Classification Search
CPC ..... C07D 213/79; C07D 213/80; A61K 31/44
See application file for complete search history.

(56) References Cited

U.S. PATENT DOCUMENTS

2013/0190315 A1* 7/2013 Metcalf .................. A61P 31/14
                                                      514/249
2014/0155427 A1   6/2014 Armani et al.

OTHER PUBLICATIONS

Banker et al., Prodrugs, Modern Pharmaceutics, Third Edition, Revised and Expanded, pp. 451 and 596 (1996).*
Bundgaard, Design of Prodrugs, p. 1, 1985.*
Silverman, Prodrugs and Drug Delivery Systems, The Organic Chemistry of Drug Design and Drug Action, pp. 352-399, 1992.*
Wolff, Some consideration for prodrug design, Burger's Medicinal Chemistry and Drug Discovery, 5th Edition, vol. 1: Principles and Practice, pp. 975-977, 1995.*
Pubchem, CID 877931, Jul. 9, 2005, pp. 1-11.

* cited by examiner

*Primary Examiner* — Deepak R Rao
(74) *Attorney, Agent, or Firm* — WC&F IP

(57) ABSTRACT

Compounds and methods for preventing and/or treating one or more symptoms of sickle cell diseases (SCD) by administering at least one of the compounds are provided. The compounds are based on vanillin which is chemically modified to increase bioavailability and activity, e.g. so that the compounds bind to the F helix of hemoglobin (Hb) and prevent adhesion of red blood cells (RBCs).

10 Claims, 11 Drawing Sheets

AROMATIC ALDEHYDES WITH SUSTAINED AND ENHANCED IN VITRO AND IN VIVO PHARMACOLOGIC ACTIVITY TO TREAT SICKLE CELL DISEASE

STATEMENT OF FEDERALLY SPONSORED RESEARCH AND DEVELOPMENT

This invention was made with government support under contract number MD009124 awarded by the National Institutes of Health. The United States government has certain rights in the invention.

BACKGROUND OF THE INVENTION

Field of the Invention

The invention generally relates to compounds that exhibit enhanced activity and stability for the treatment of sickle cell disease (SCD). In particular, the compounds are vanillin-based aromatic aldehydes in which the alcohol moiety is converted into aryl or alkyl amides and esters or inorganic phosphate esters, and in which the aldehyde functional (CHO) group is optionally replaced by a protected aldehyde moiety (promoiety).

Description of Related Art

Hemoglobin (Hb) functions to oxygenate tissue by equilibrating between two allosteric states: a tense (T) state, which exhibits low-affinity for ligand, and a relaxed (R) state, which exhibits high affinity for ligand.[1] Sickle cell disease (SCD) is an inherited hematologic disorder and occurs as a result of replacement of βGlu6 and βVal6 in Hb, forming sickle Hb (Hb S).[2] Under hypoxia or low oxygen ($O_2$) tension, which leads to an increased concentration of the low-affinity deoxygenated (T-state) Hb, Hb S polymerizes into long, rigid, and insoluble fibers resulting in sickling of red blood cells (RBCs). The polymer which is initiated by the primary interaction involving βVal6 is stabilized by several other secondary contacts between the Hb S molecules.[3] Hypoxia-induced sickling leads to several secondary pathophysiological events, e.g. adhesion of RBCs to tissue endothelium, oxidative stress/damage, hemolysis (rupture) of RBCs, inflammation, vaso-occlusion, impaired microvascular blood flow, decreased vascular nitric oxide bioavailability, painful crises, morbidity and mortality.[4] The only drugs currently approved for treating SCD are hydroxyurea (HU) and more recently, Endari™ (L-glutamine oral powder). HU induces γ-globin expression to form fetal Hb (HbF).[5] However, not all patients respond to HU and/or Endari™, and HU can cause myelosuppression, a life-threatening side effect. Furthermore, the drug remains inaccessible in many parts of the world. The need for alternate modes of therapy remains extremely pressing, especially in the face of the significant mortality, morbidity, healthcare disparities and public health burden imposed by SCD.

Vanillin (FIG. 1) and several of its analogs and derivatives have previously been studied for their antisickling activity.[1,6,7] Specifically, the compounds form Schiff-base adduct with Hb to stabilize the high-affinity oxygenated R-state Hb (in the R2 conformation) relative to the low-affinity deoxygenated T-state Hb, resulting in increase in Hb affinity for oxygen. By increasing Hb affinity for oxygen, the compounds prevent the hypoxia-induced primary pathophysiology of Hb S polymerization and RBC sickling, and concomitantly ameliorate several of the cascading secondary adverse events. Schiff-base interaction between the compound's aldehyde group and the N-terminal valine amino group of a globin chains (Val1) exists in equilibrium between bound adduct complex and unbound Hb and free compound. For a stable Schiff-base complex and consequently an effective pharmacologic outcome, these compounds should make strong interactions with Hb, and exhibit a slow rate of dissociation. Vanillin does not form strong interactions with the protein, and consequently its dissociation from the protein is fast, consistent with vanillin's sub-optimal biological activity. In addition to vanillin's weak interactions with the protein, it also undergoes significant metabolism of the aldehyde, which is the active component of the molecule, resulting in poor pharmacokinetic properties, including lack of bioavailability.

The crystal structures of vanillin and several of its analogs and derivatives have been elucidated to explain how binding of these molecules leads to stabilization of the R-state Hb and consequently reduces or prevents hypoxia-induced Hb S polymerization and RBC sickling.[1,8] Based on these previous studies, a new generation of compounds (termed TD) were developed by coupling a hydroxylmethyl pyridinyl to the benzaldehyde of the vanillin (FIG. 1). Although the TD compounds showed a significantly more potent effect than vanillin, like vanillin, these compounds also undergo significant metabolism leading to sub-optimal pharmacokinetic properties, e.g. short duration of pharmacologic action and low bioavailability. These properties would necessitate the use of frequent and very high doses of such compounds, which is undesirable for treatment of a chronic disease, and hence their development has not been pursued.

There is a pressing need to develop new anti-sickling agents that bind with higher affinity to Hb and do not undergo significant metabolism, that exhibit a long duration of pharmacologic action and have a high level of bioavailability.

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

Provided herein are new, potent anti-sickling agents that have sustained and enhanced antisickling pharmacologic activity in vitro and in vivo, compared to prior art compounds. Activity is sustained due to resistance to in vivo metabolism and activity is increased due to a dual antisickling mechanism of action: i) the compounds increase Hb affinity for oxygen and ii) directly destabilize polymers formed by sickled RBCs. These are critical properties for a drug that is repeatedly administered to treat a chronic condition such as sickle cell anemia.

It is an object of this invention to a vanillin-derived compound having Formula I:

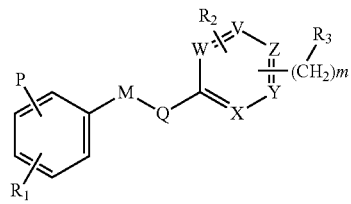

where R1 and R2 are the same or different and are H; hydroxyl; halogen; or a substituted or unsubstituted: alkyl, alkoxy, aryl, O-aryl, cycloalkane or heterocycle; R3 is alkyl ester, aryl ester, alkylamide, arylamide, phosphate or sulfate; M and Q are the same or different and are O or $(CH_2)_n$ where $n=0-6$; X, Y, Z, W and V are the same or different and are independently H, C, N, S or O; $m=0-6$, and P=CHO or a promoiety; or a pharmaceutically acceptable salt thereof. In some aspects, the vanillin-derived compound is designed to bind to the F helix of hemoglobin (Hb). In additional aspects, P is CHO. In further aspects, P is a protected aldehyde group or promoiety. In other aspects, the promoiety is

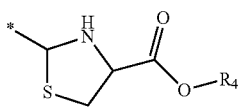

where R4 is H or a linear or branched C1-C5 alkyl; and where the bond marked with * bonds directly to a carbon of the benzene ring. In yet further aspects, the vanillin-derived compound is selected from the group consisting of:

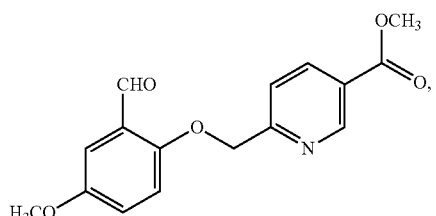

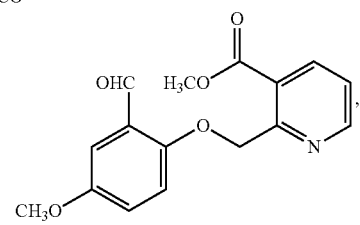

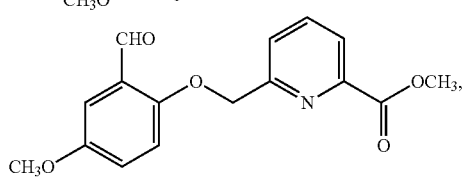

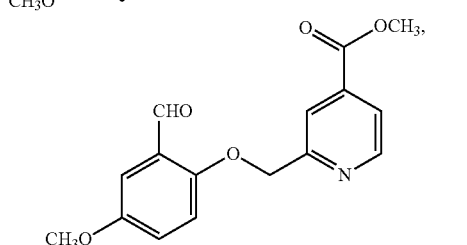

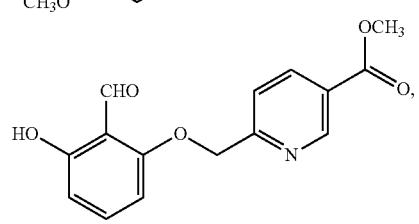

-continued

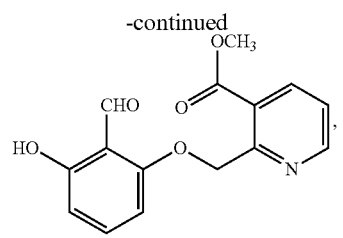

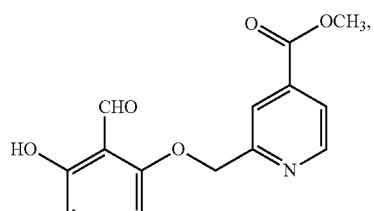

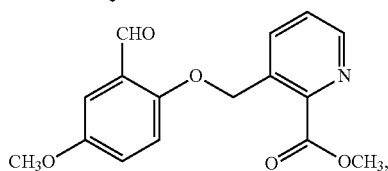

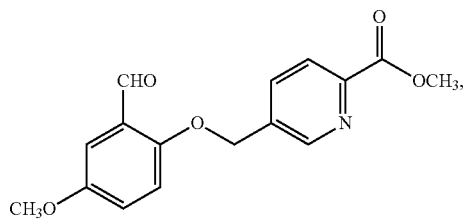

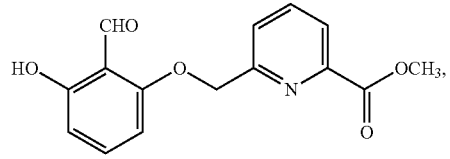

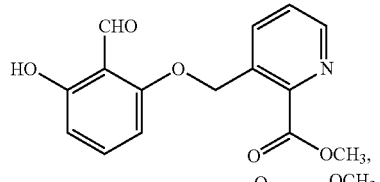

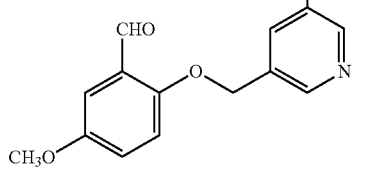

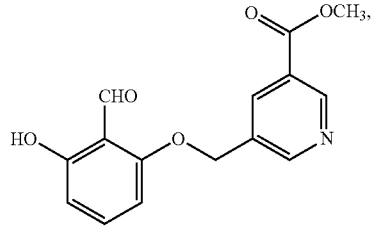

-continued

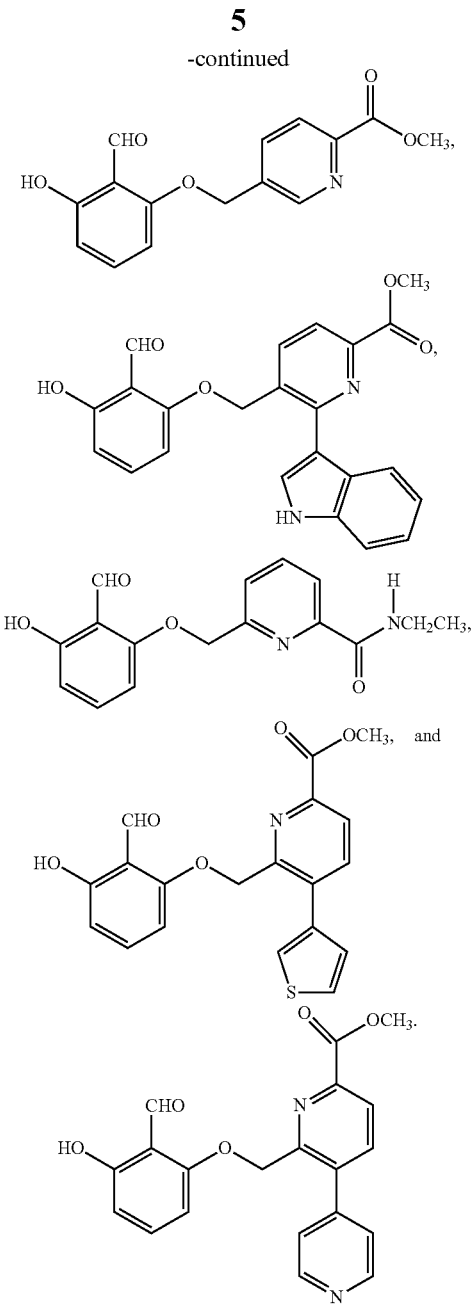

In additional aspects, the vanillin-derived compound is

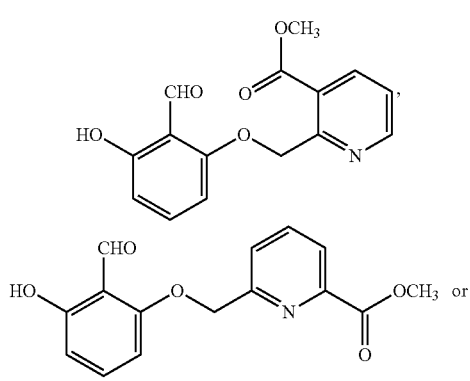

-continued

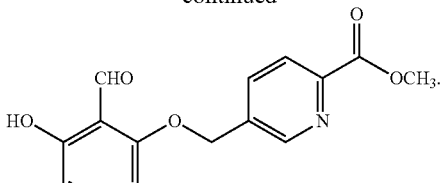

In yet further aspect, the vanillin-derived compound is

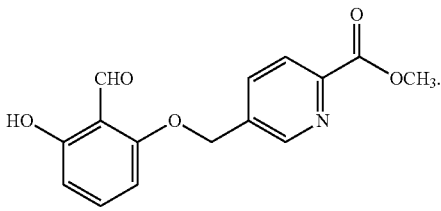 [SMILES: COC(=O)c1ccc(COc2cccc(O)c2C=O)cn1]

In some aspects, the vanillin-derived compound is a HCl salt.

Also provided is a composition comprising at least one vanillin-derived compound as disclosed herein. In some aspects, the composition is in a form for oral administration.

Also provided is a method of preventing or treating one or more symptoms or conditions of sickle cell disease (SCD) in a subject in need thereof, comprising administering to the subject a therapeutically effective amount of at least one vanillin-derived compound as disclosed herein. In some aspects, the one or more symptoms or conditions of SCD are selected from the group consisting of HbS polymerization, red blood cell (RBC) sickling, adhesion of RBCs to tissue endothelium, oxidative stress and/or damage, hemolysis of RBCs, inflammation, vaso-occlusion, impaired microvascular blood flow, a decrease in vascular nitric oxide bioavailability, pain, and death. In some aspects, the step of administering is performed orally.

Also provided is a method of preventing or treating one or more symptoms of hypoxia in a subject in need thereof, comprising administering to the subject a therapeutically effective amount of at least one vanillin-derived compound disclosed herein. In some aspects, the step of administering is performed orally.

DETAILED DESCRIPTION

Figure 1:
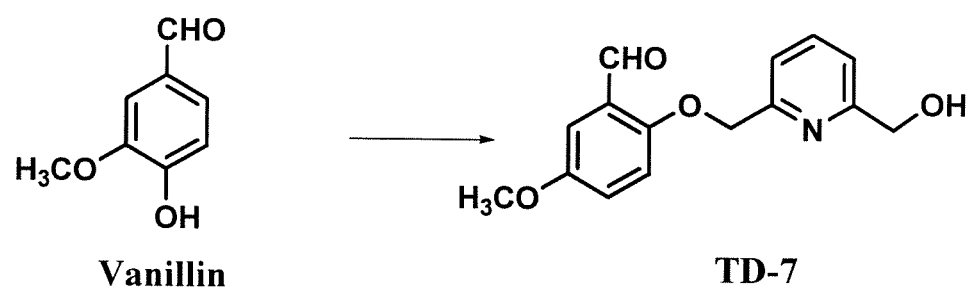
FIG. 1: Structures of vanillin and a prototype TD compound, TD-7.

Disclosed herein are vanillin-based compounds in which an alcohol moiety on the pyridine ring is modified into aryl or alkyl amides and esters or inorganic phosphate esters. This derivatization renders the alcohol resistant to in vivo metabolism, leading to more sustained and enhanced pharmacologic activities. In addition, the bulky ester or amide moiety of these novel compounds makes novel interactions with the F helix of Hb. As a result, these compounds exhibit a dual antisickling mechanism of action: 1) the compounds increase the affinity of HbS for oxygen, making less HbS available for sickling; and 2) the compounds interfere directly with HbS polymer formation. In addition, the CHO group of vanillin is optionally replaced by a protected aldehyde group (promoiety, pharmacophore), thereby forming e.g. a prodrug to further increase bioavailability. A pharmacophore is a part of a molecular structure or compound that is responsible for a particular biological or pharmacological interaction.

As noted in the Background section above, hypoxia or low oxygen ($O_2$) tension leads to an increased concentration of low-affinity deoxygenated (T-state) Hb. The compounds disclosed herein bind to liganded HbS and hold the target protein in a high-affinity oxygenated (relaxed) state thereby decreasing the concentration of deoxygenated HbS, as well as preventing premature and fast release of the bound oxygen prior to liganded Hb reaching tissue beds.

Furthermore, deoxygenated HbS typically polymerize into long, rigid, and insoluble fibers, resulting in sickling of red blood cells (RBCs). The F helix of HbS is very important in stabilizing these polymers through secondary interactions with adjacent HbS. Without being bound by theory, it is believed that the bulky ester or amide moieties, or the charged sulphate or phosphate groups of the compounds interact with the surface located F helix of Hb, and this interaction leads to stereospecific inhibition of polymer formation by HbS. In other words, binding of these ligands to the F helix induces a conformation change, occludes the F helix, and abrogates interactions between HbS, thereby weakening the polymer and preventing sickling.

The Compounds

Compounds disclosed herein are based on or derived from vanillin. The compounds, or a functional group or substituent of the compounds (e.g. the ester, amide, sulphate or phosphate groups) binds to the F helix of hemoglobin (Hb) and prevents or decreases the interaction between HbS molecules and thus prevent sickling of red blood cells (RBCs).

The compounds have a generic Formula I:

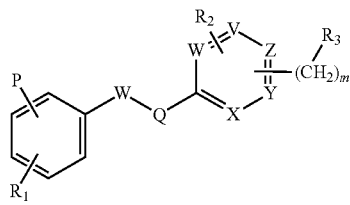

wherein:
R1 and R2 are the same or different and are H; hydroxyl; halogen; or substituted or unsubstituted: alkyl, alkoxy, aryl, O-aryl, cycloalkyl or heterocyclic;
R3 is an alkyl ester, aryl ester, an alkylamide, an arylamide, phosphate or sulfate;
M and Q are the same or different and are O or $(CH_2)n$ where n=0-6 (e.g. 0, 1, 2, 3, 4, 5, or 6);
X, Y, Z, W and V are the same or different and are (independently) H, C, N, S or O;
m=0-6 (e.g. 0, 1, 2, 3, 4, 5, or 6), and
P=CHO or a promoiety.
Pharmaceutically acceptable salts of the compounds are also encompassed.
Examples of suitable promoieties include but are not limited to the thiazolidine:

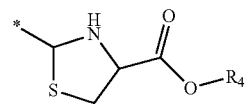

where R4 is H or a linear or branched C1-C5 alkyl, and where the bond marked with * bonds directly to a carbon of the benzene ring. Other means of protecting the aldehyde, include but not limited to conversion of the aldehyde to the corresponding imine, acetal, hemiacetal, ester, or alcohol.

Exemplary halogens include but are not limited to: Cl, Br, I and F.

Exemplary alkyl groups include but are not limited to: linear or branched C1-C12 alkyl e.g. methyl, ethyl, propyl, isopropyl, butyl (e.g. n-butyl, secondary butyl, isobutyl, tertiary butyl), pentyl (e.g. n-pentyl, tert-pentyl, neopentyl, isopentyl, sec-pentyl, 3-pentyl), hexyl, etc.) each of which may be substituted or unsubstituted. The alkyl group may be optionally substituted with one, two, or three substitutents, or, in the case of alkyl groups of two carbons or more, four substituents e.g. alkoxy, alkylsulfayl, amino, azido, halo, heterocyclyle)oxy, hydroxyl, nitro, oxo, thioalkoxy, thiol, etc.

Alkoxy refers to an alkyl group singularly bonded to oxygen (R—O), i.e. an alkyl group having an oxygen radical attached thereto. In some aspects, the R group of the alkoxy is a ($C_1$-$C_{12}$) alkyl (see above for exemplary alkyls) having an oxygen radical attached thereto. Exemplary alkoxy groups include but are not limited to: methoxy, ethoxy, propoxy (e.g., n-propoxy and isopropoxy), t-butoxy, and the like, each of which may be substituted or unsubstituted. In some embodiments, the alkyl group or cyclic alkyl ring can be further substituted with 1, 2, 3, or 4 substituent groups as defined herein (e.g., O, hydroxyl, alkoxy, etc.).

As used herein, "aryl" refers to any functional group or substituent that is or is derived from an aromatic ring, e.g.

an aryl is a radical derived from an aromatic hydrocarbon by removal of a hydrogen atom. The aromatic hydrocarbon may be heteroaromatic (one or more atoms in the ring is/are not carbon and are instead e.g. O, N, S, etc.); polycyclic (containing two or more aromatic rings); or substituted (aromatic rings having other functional groups attached, e.g. alkyl, alkenyl, phenyl, aldehyde, hydroxyl, sulfhydryl, carboxyl, carbonyl, amide, amine, nitrate, sulfate, phosphate, pyridyl, etc.). Examples of aryl groups include but are not limited to: an aromatic hydrocarbon such as phenyl, naphthyl, thienyl, indolyl, tolyl, furyl, pyridyl, anthracenyl, fluorenyl, indanyl, indenyl, etc. each of which may be heteroaromatic and/or substituted or unsubstituted.

"O-aryl" refers to an oxygen atom bonded to an aryl group, as described above, i.e. a radical derived from an aromatic hydrocarbon by removal of a hydrogen atom. O-aryl groups which are used in the compounds described herein include but are not limited to those listed above for aryl, each of which may be substituted or unsubstituted.

A cycloalkane is a cyclic compound in which all atoms of the ring (or rings) are C and the bonds between C atoms are saturated. As used herein, cycloalkyl refers to the radical (form that has an unpaired valence electron) and can form a bond with another entity. Cycloalkyl compounds may be unicyclic or polycyclic (e.g. bicyclic, tricyclic, etc.); and polycyclic substituents comprising more (e.g. 4, 5, 6, etc.) rings are also encompassed. If the system is polycyclic, the rings in the systems may have the same number of atoms (e.g. a bicyclic ring comprising two 6-membered rings); or the rings of the system may have two different types of rings (e.g. a bicyclic ring comprising one 6-membered ring and one 5-membered ring), and may be e.g. fused or bridged. Examples of cycloalkyls include but are not limited to: cyclopropyl, cyclobutyl, cyclopentyl, cyclohexyl, cycloheptyl, cyclooctyl, butyl, cyclopentyl, hexyl, heptyl, octyl, etc., and polycyclic combinations of these such as: decalin, camphorquinone, polyquinane, and the like. The cycloalkyl may be substituted or unsubstituted.

A heterocyclic compound or ring structure is a cyclic compound (e.g. a cycloalkane or aryl compound) that has atoms of at least two different elements as members of its ring(s). Generally, each ring of the system has about 4, 5, 6, or 7 atoms, at least one of which is carbon, and at least one of which is not carbon. For example, 1 or 2 atoms may be non-carbon atoms while the rest are carbon atoms. The rings may or may not contain double bonds, e.g. one or more C=C bonds. The heteroatoms are, for example, N, O, P or S, but other heteroatoms are not excluded. Exemplary heterocyclic systems are unicyclic, bicyclic or tricyclic; however, systems comprising more rings are also encompassed. If the system is multicyclic, the rings in the systems may have the same number of atoms (e.g. a bicyclic ring comprising two 6-membered rings) and the two rings may be the same or different; or the rings of the system may have two different types of rings (e.g. a bicyclic ring comprising one 6-membered ring and one 5-membered ring). Examples of heterocyclic systems that may be present in the compounds disclosed herein include but are not limited to: oxazole, pyrazoline, imidazole, pyrazole, pyrazine, purine, indoline, quinolone, pteridine, indene, piperidine, tetrahydrofuran, pyridine, pyrimidine, thiophene, pyrrole, furan, quinoline, benzothiophene, indole, benzofuran, heterocycles comprising two substituted benzene rings such as acridine, dibenzothiophene, carbazole, dibenzofuran, etc.

Alkyl esters and aryl esters are esters (chemical compounds derived from an organic or inorganic acid in which at least one —OH (hydroxyl) group is replaced by an —O-alkyl (alkoxy) group or an —O-aryl group, with the alkyl and aryl portions being those defined above.

Alkylamides and arylamide are amides (acid derivatives with the general formula R'—CO—NH$_2$, where R' is an alkyl or aryl group as described above.

Pharmaceutically acceptable salts of the compounds are also encompassed. Examples of such salts include, but are not limited to, salts formed with inorganic acids (for example, hydrochloric acid (HCl), hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, palmoic acid, alginic acid, polyglutamic acid, naphthalenesulfonic acid, naphthalenedisulfonic acid, methanesulfonic acid, p-toluenesulfonic acid and polygalacturonic acid. Other salts include pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

Exemplary Compounds

Exemplary compounds of the invention include but are not limited to:

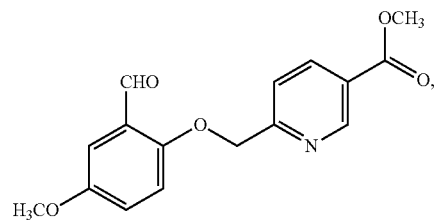

Figure 2:
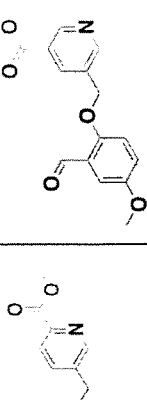
FIG. 2: Structures of exemplary "PP" compounds.

("PP1" in FIG. 2)

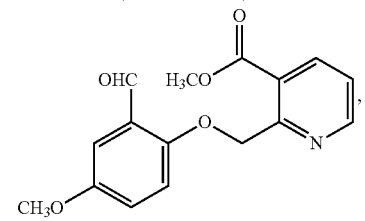

("PP2" in FIG. 2)

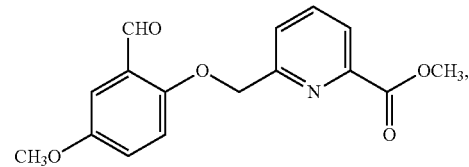

("PP3" in FIG. 2)

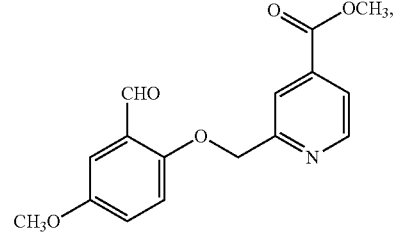

("PP4" in FIG. 2)

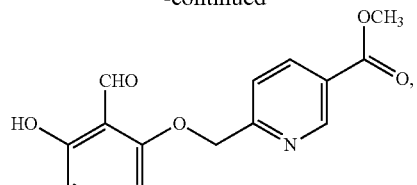
("PP5" in FIG. 2)
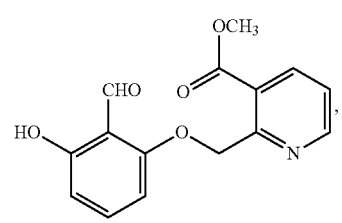
("PP6" in FIG. 2)
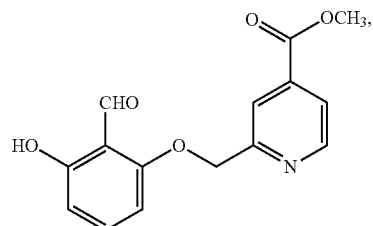
("PP7" in FIG. 2)
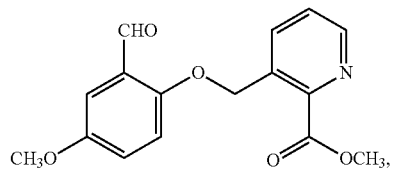
("PP8" in FIG. 2)
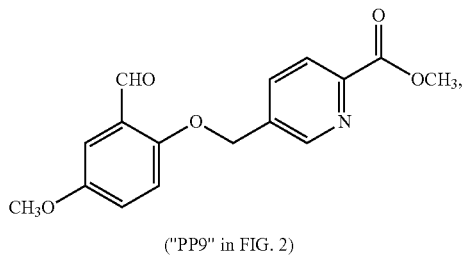
("PP9" in FIG. 2)
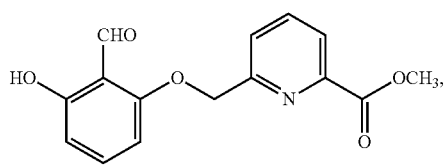
("PP10" in FIG. 2)
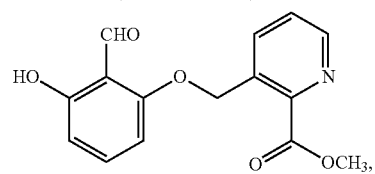
("PP11" in FIG. 2)
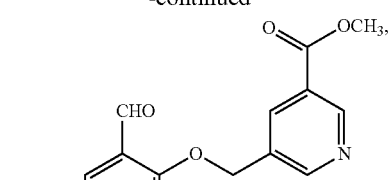
("PP12" in FIG. 2)
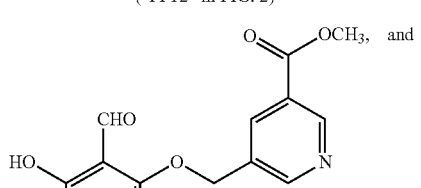
("PP13" in FIG. 2)
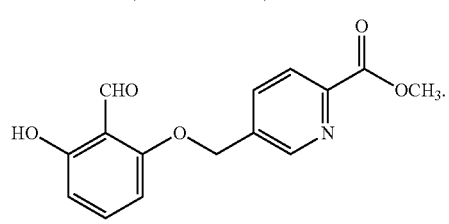
("PP14" in FIG. 2)
Additional exemplary compounds include but are not limited to:
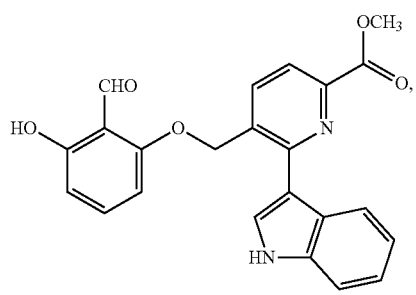
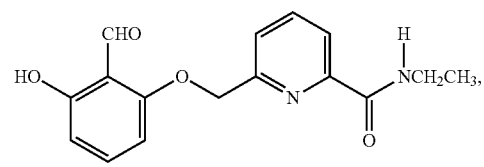
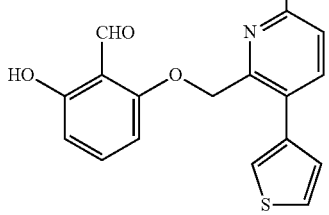

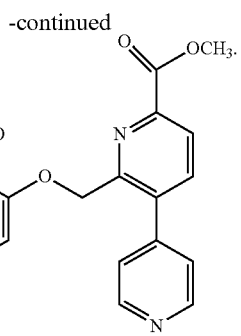

Mechanistically, these compounds increase the hemoglobin oxygen affinity and concomitantly exhibit antisickling activity in part via a Schiff-base interaction between the aldehyde moiety and the N-terminal αVal1 nitrogen of relaxed state hemoglobin. Like all aldehydes, the aldehyde moiety of the compounds is susceptible to rapid and significant metabolism, e.g. by aldehyde dehydrogenase, into the inactive carboxylate derivative that could potentially shorten the compounds pharmacologic effect. Consistently, several aromatic aldehyde antisickling agents, e.g. 5-HMF have failed in human clinical studies because of such metabolic shortcomings. To overcome such potential disruptive metabolism, in some aspect, the aldehyde group of the compounds presented herein is protected, e.g. via a coupling reaction with L-cysteine to form the thiazolidine complex (Zhang et al. Br J Haematol. 2004; 125:788-795). The promoiety or prodrug compounds exhibit improved bioavailability and/or a longer half-life due to decreased aldehyde metabolism. This permits the drugs to be administered i) at lower doses and/or ii) less frequently, while still maintaining the beneficial therapeutic effects of the unprotected aldehyde, thereby minimizing side effects and/or increasing patient compliance with administration.

Thus, in some aspects, the compounds described and depicted above may be further rendered resistant to in vivo metabolism by replacing the CHO functional group with a protecting group. Examples of suitable promoieties (pharmacophores) include but are not limited to

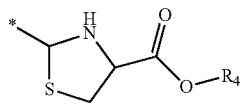

where R4 is H or a linear or branched C1-C5 alkyl; and where the bond marked with * bonds directly to a carbon of the benzene ring. An example of this promoiety is that which is formed when L-cysteine forms a thiazolidine complex:

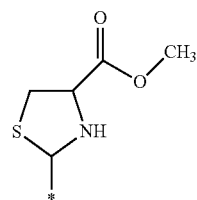 [SMILES: *C1NC(C(=O)OC)CS1]

where * indicates the point of attachment to C of the benzene ring. Other routes to form the thiazolidine, include but not limited to the use of cysteamine and amino thiol.

Other means of protecting the aldehyde include but are not limited to conversion of the aldehyde to the corresponding imine, acetal, hemiacetal, ester, or alcohol.

Examples of compounds that comprise a promoiety include but are not limited to:

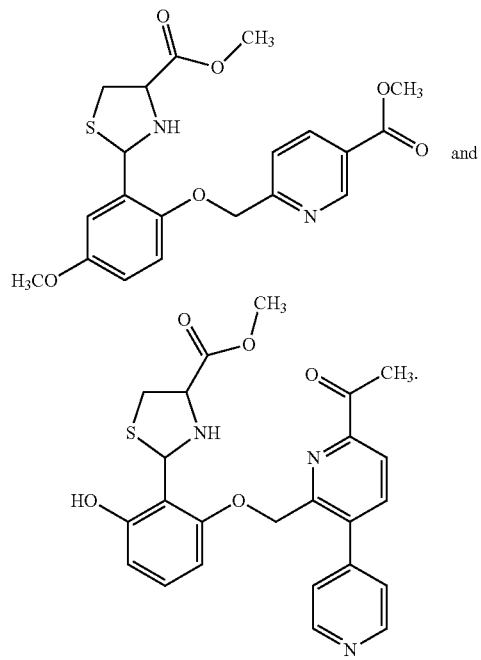

A promoiety may be included in or on any of the compounds disclosed herein.

Advantages of the Compounds

The compounds described herein exhibit improved pharmacologic activity, i.e. more potency and/or increased (lengthened, longer-lasting, etc.) half-lives, and/or improved bioavailability under physiological conditions (e.g. in circulation, in plasma, etc.) compared to other vanillin-based compounds. For example, the compounds exhibit in vivo half-lives of at least about 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5 or 12.0 hours, or even longer, e.g. about 12 to 36 hours, i.e. about 12, 14, 16, 18, 20, 22, 24, 26, 28, 30, 32, 34 or 36 hours. In some aspects, compared to vanillin or TD, the compounds exhibit 1, 2, 3, 4, 5, 6, 7, 8, 9, or 10-fold or more greater potency in terms of preventing the HbS sickling and/or the formation of sickled HbS polymers. Thus, in some aspects, the compositions comprising the compounds are administered less frequently and/or at lower doses than would be required for prior art compounds, yet the same or an increased level of beneficial effects is experienced by subjects receiving the compounds.

Exemplary Methods of Treatment Using the Prodrugs or Derivatives

The compounds described herein are used to treat or prophylactically treat diseases and/or conditions related to hypoxia, such as SCD and other diseases/conditions described below. As used herein, "prophylactically treat" ("prophylactic treatment", "prophylactically treating" etc.) and "prevent" ("prevention", "preventing" etc.) refer to warding off or averting the occurrence of at least one symptom of a disease or unwanted condition (such as at least one symptom of SCD), by prophylactic administration of a composition comprising at least one compound as described herein, to a subject in need thereof. Generally, "prophylactic" or "prophylaxis" relates to a reduction in the likelihood of the patient developing a disorder or a symptom of a disorder. Typically, the subject is considered by one of skill in the art to be at risk of or susceptible to developing at least one symptom of the disease or unwanted condition, or is considered to be likely to develop at least one symptom of the disease/condition in the absence of medical intervention. In some aspects, for "prevention" or "prophylactic treatment", administration occurs before the subject has, or is known or confirmed to have, symptoms of the disease (condition, disorder, syndrome, etc.; unless otherwise indicated, these terms are used interchangeably herein). In other words, symptoms may not yet be overt or observable, or may be very "early stage" symptoms. The subject may be considered at risk due to a variety of factors, including but not limited to: genetic predisposition; evidence of "early" symptoms; tests such as blood tests, etc. In such aspects, treatment of the subject may prevent the noxious or harmful effects or outcomes (results) of full blown disease. "Prevention" or "prophylactic treatment" of a disease or condition may involve completely preventing the occurrence of detectable symptoms, or, alternatively, may involve lessening or attenuating the degree, severity or duration of at least one symptom of the disease that would otherwise occur in the absence of the medical interventions provided herein.

"Treat" (treatment, treating, etc.) as used herein refers to administering at least one composition comprising a compound as described herein, to a subject that already exhibits at least one symptom of a disease such as SCD. In other words, at least one parameter that is known to be associated with the disease has been measured, detected, experienced or observed in the subject. For example, the symptom may be the primary pathophysiology of hypoxia-induced RBC sickling associated with sickle cell disease. In addition, the compounds disclosed herein ameliorate several of the cascading secondary adverse events of SCD, including adhesion of RBCs to tissue endothelium, oxidative stress, hemolysis of RBCs, decreased vascular NO bioavailability, vaso-occlusion, impaired microvascular blood flow, increased blood pressure, and painful crises, e.g. due to polymerization of RBCs. For example, the compounds generally do one or more of the following: increase $O_2$-affinity of HbS; decrease fiber formation; reduce sickle cell mechanical fragility; reduce RBC hemolysis; attenuate hypoxia-induced cell necrosis and apoptosis; improve microvascular function (e.g. during recovery from hemorrhagic shock); results in hemodynamic and oxygenation benefits during hypoxia (e.g. maintenance of blood pressure and heart rate; preservation of microvascular blood flow; reduction in heart and brain hypoxia areas); reduce pain; decrease lactate dehydrogenase and/or RBC hemolysis; reduce diastolic blood pressure; increase blood oxygen levels ($S_pO_2$) during hypoxia challenge; etc.

"Treatment" of a disease involves the lessening or attenuation, or in some instances, the complete eradication, of at least one symptom of the disease that was present prior to or at the time of administration of the composition.

Exemplary Compositions and Methods of Administration

Provided herein are compositions comprising at least one compound as described herein, and methods of administering the same to treat e.g. SCD, hypoxia, etc. Implementation of the methods generally involves identifying patients suffering from or at risk of developing a disease or condition described herein (for example SCD or hypoxia), and administering a composition as described herein by an appropriate route. The exact dosage to be administered may vary depending on the age, gender, weight and overall health status of the individual patient, severity of disease symptoms, or on other treatments being received by the patient, as well as the extent or progression of the disease condition being treated and the precise etiology of the disease. However, in general for administration to mammals (e.g. humans), sufficient composition is administered to achieve dosages in the range of from about 0.1 to about 1000 mg or more per kg of body weight per 24 hr., e.g. from about 1 to about 500 mg, 5 to 100, or 10-50 mg per kg of body weight per 24 hr. Generally, a therapeutically effective dose is from about 50 to about 150 mg per kg of body weight per 24 hr. The dose will vary with the route of administration, the bioavailability, and the particular formulation that is administered, as well as according to the nature of the malady that is being prevented or treated.

The compositions are generally administered in a pharmaceutically acceptable formulation which includes suitable excipients, elixirs, binders, and the like (generally referred to as "pharmaceutically and physiologically acceptable carriers"), which are pharmaceutically acceptable and compatible with the active ingredients. The prodrugs or derivatives may be present in the formulation as pharmaceutically acceptable salts (e.g. alkali metal salts such as sodium, potassium, calcium or lithium salts, ammonium, etc.) or as other complexes. It should be understood that the pharmaceutically acceptable formulations include solid, semi-solid, and liquid materials conventionally utilized to prepare solid, semi-solid and liquid dosage forms such as tablets, capsules, liquids, aerosolized dosage forms, and various injectable forms (e.g. forms for intravenous administration), etc. Suitable pharmaceutical carriers include but are not limited to inert solid diluents or fillers, sterile aqueous solutions and various organic solvents. Examples of solid carriers (diluents, excipients) include lactose, starch, conventional disintegrating agents, coatings, lactose, terra alba, sucrose, talc, gelatin, agar, pectin, acacia, magnesium stearate, stearic acid and lower alkyl ethers of cellulose. Examples of liquid carriers include but are not limited to various aqueous or oil based vehicles, saline, dextrose, glycerol, ethanol, isopropanol, phosphate buffer, syrup, peanut oil, olive oil, phospholipids, fatty acids, fatty acid amines, polyoxyethylene, isopropyl myristate, ethyl cocoate, octyl cocoate, polyoxyethylenated hydrogenated castor oil, paraffin, liquid paraffin, propylene glycol, celluloses, parabens, stearyl alcohol, polyethylene glycol, isopropyl myristate, phenoxyethanol, and the like, or combinations thereof. Water may be used as the carrier for the preparation of compositions which may also include conventional buffers and agents to render the composition isotonic. Oral dosage forms may include various thickeners, flavorings, diluents, emulsifiers, dispersing aids, binders, coatings and the like. The composition of the present disclosure may contain any such additional ingredients so as to provide the composition in a form suitable for the intended route of administration. In addition, the composition may contain minor amounts of auxiliary substances such as wetting or emulsifying agents, pH buffering agents, and the like. Similarly, the carrier or diluent may include any sustained release material known in the art, such as glycerol monostearate or glycerol distearate, alone or mixed with wax. Other potential additives and other materials (preferably those which are generally regarded as safe [GRAS]) include: colorants; flavorings; surfactants (TWEEN®, oleic acid, etc.); and solvents, stabilizers, binders or encapsulants (lactose, liposomes, etc.). Preservatives such as methyl paraben or benzalkium chloride may also be used. Depending on the formulation, it is expected that the active components (e.g. at least one prodrug or derivative) will be present at about 1% to about 99% of the composition and the vehicular "carrier" will constitute about 1% to about 99% of the composition. The pharmaceutical compositions of the present disclosure may include any suitable pharmaceutically acceptable additives or adjuncts to the extent that they do not hinder or interfere with the therapeutic effect(s) of the composition. Still other suitable formulations for use in the present disclosure can be found, for example in Remington's Pharmaceutical Sciences 22nd edition, Allen, Loyd V., Jr editor (September 2012); and Akers, Michael J. Sterile Drug Products: Formulation, Packaging, Manufacturing and Quality; publisher Informa Healthcare (2010).

The compositions (preparations) of the present disclosure are formulated for administration by any of the many suitable means which are known to those of skill in the art, including but not limited to: orally, by injection, rectally, by inhalation, intravaginally, intranasally, topically, as eye drops, via sprays, transdermally, sublingually, by rectal and buccal delivery, by inhalation of an aerosol, by microneedle delivery, etc. In some aspects, the mode of administration is oral, by injection or intravenously, preferably via an orally administered pill.

The administration of the compound of the present disclosure may be intermittent, or at a gradual or continuous, constant or controlled rate (e.g. in a sustained release formulation which further extends the time of bioavailability). In addition, the time of day and the number of times per day that the pharmaceutical formulation is administered vary and are best determined by a skilled practitioner such as a physician. Generally, the compounds are administered at least once a day, and may be administered e.g. 2, 3, 4, or more times per day. During a crisis, administration may be more frequent, e.g. continuously via IV.

Administration of the compound by any means may be carried out as a single mode of therapy, or in conjunction with other therapies and treatment modalities, e.g. antibiotics, pain medication, hydroxyurea, vaccinations, blood transfusions, provision of supplemental oxygen, gene therapy, nitric oxide, drugs to boost fetal hemoglobin production, statins, vanillin, TD compounds, etc. In addition, if hypoxia due to a heart condition is the indication, then additional treatments for heart disease may be provided, including surgery. Other treatment options include various neutraceuticals, diet regimens, exercise, etc. "In conjunction with" refers to both administration of a separate preparation of the one or more additional agents, and to inclusion of the one or more additional agents in a composition of the present disclosure.

The subject to whom the composition is administered is generally a mammal, frequently a human, but this is not always the case. Veterinary applications of this technology are also contemplated, e.g. for companion pets (cats, dogs, etc.), or for livestock and farm animals, for horses, and even for "wild" animals that have special value or that are under the care of a veterinarian, e.g. animals in preserves or zoos, injured animals that are being rehabilitated, etc.

Diseases and Conditions That are Treated

In some aspects, the disease or condition that is prevented or treated as described herein is sickle cell disease and pathophysiologies associated with SCD, such as hypoxia-induced RBC sickling. In addition, the compounds ameliorate cascading secondary adverse events, including adhesion of RBCs to tissue endothelium, oxidative stress, hemolysis of RBCs, decreased vascular NO bioavailability, vaso-occlusion, impaired microvascular blood flow, increased blood pressure, and painful crises. In addition, the compounds increase $O_2$-affinity of HbS, decrease fiber formation, reduce sickle cell mechanical fragility, increase blood oxygen levels ($SpO_2$) and reduce RBC hemolysis.

In other aspects, the compounds are used to treat or prevent symptoms of hypoxia that is or is not related to SCD. As used herein hypoxia (also known as hypoxiation) is a condition in which the body or a region of the body is deprived of adequate oxygen supply at the tissue level. Hypoxia is classified as either generalized, affecting the whole body, or local, affecting a region of the body. There are four types of hypoxia: (1) the hypoxemic type, in which the oxygen pressure in the blood going to the tissues is too low to saturate the hemoglobin; (2) the anemic type, in which the amount of functional hemoglobin is too small, and hence the capacity of the blood to carry oxygen is too low; (3) the stagnant type, in which the blood is or may be normal but the flow of blood to the tissues is reduced or unevenly distributed; and (4) the histotoxic type, in which the tissue and/or cells are poisoned and are therefore unable to make proper use of oxygen. Diseases of the blood, the heart and circulation, and the lungs may all produce some form of hypoxia.

Generalized hypoxia occurs, for example, in healthy people when they ascend to high altitude, where it causes altitude sickness leading to potentially fatal complications such as high altitude pulmonary edema (HAPE) and high altitude cerebral edema (HACE). Hypoxia also occurs in healthy individuals when breathing mixtures of gases with a low oxygen content, e.g. while diving underwater or when in outerspace, and especially when using closed-circuit rebreather systems that control the amount of oxygen in the supplied air. Hypoxia also occurs as a consequence of preterm birth in the neonate due to immature lung development. Hypoxia resulting from ischemia (insufficient blood flow to a tissue or organ), is referred to as 'ischemic hypoxia' and is caused by e.g. an embolic event, a heart attack that decreases overall blood flow, or trauma to a tissue that results in damage, or may be purposefully induced in some medical procedures, e.g. implantation of a stent, application of a tourniquet, etc. Diseases such as peripheral vascular disease can cause local hypoxia. Other causes include alterations in respiratory drive, such as in respiratory alkalosis, physiological or pathological shunting of blood, diseases interfering in lung function resulting in a ventilation-perfusion mismatch, such as a pulmonary embolus, or alterations in the partial pressure of oxygen in the environment or lung alveoli. When hemoglobin is deficient, anemia can result and can cause 'anaemic hypoxia' if tissue perfusion is decreased. Carbon monoxide poisoning can cause hypoxia, either acutely, as with smoke intoxication, or over a period of time, as with cigarette smoking or exposure to smog. Certain odorless asphyxiant gases (e.g. nitrogen, methane, etc.) induce hypoxia as does cyanide poisoning and the formation of methemoglobin e.g. by ingesting sodium nitrite or certain other drugs and chemicals. The compounds described herein are used to prevent or treat symptoms of one or more of any of these hypoxia-related conditions. In addition, the compounds attenuate hypoxia-induced cell necrosis and apoptosis, improve microvascular function during resuscitation from hemorrhagic shock, result in hemodynamic and oxygenation benefits during hypoxia (e.g. maintenance of blood pressure and heart rate; preservation of microvascular blood flow; reduction in heart and brain hypoxia areas, etc.), and provide improvement in several clinical symptoms, including reduced pain, decreased lactate dehydrogenase and/or RBC hemolysis, reduction in diastolic blood pressure, and an increase in blood oxygen levels ($S_pO_2$) during hypoxia challenge.

Methods of Making the Compounds

A generic scheme for making the compounds disclosed herein is depicted below in Scheme I:

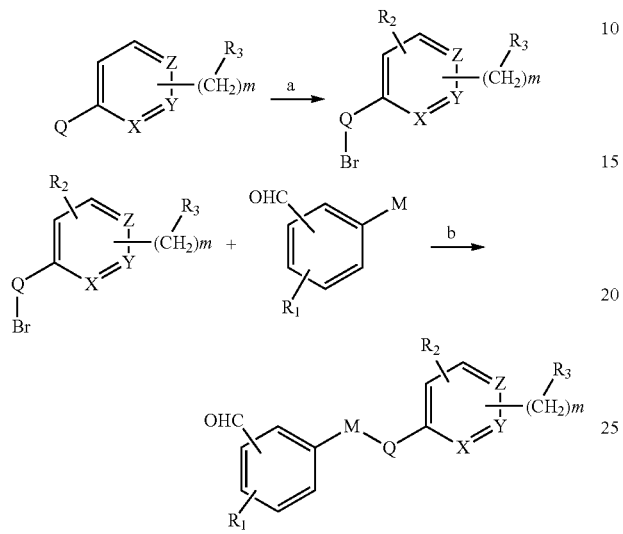

where R1 and R2 are the same or different and are H; hydroxyl; halogen; or substituted or unsubstituted: alkyl, alkoxy, aryl, O-aryl, cycloalkane or heterocycle; R3 is an alkyl ester, aryl ester, an alkylamide, an arylamide, phosphate or sulfate; M and Q are the same or different and are O or $(CH_2)n$, where n=0-6 (e.g. 0, 1, 2, 3, 4, 5, or 6); X, Y, Z, W and V are the same or different and are (independently) H, C, N, S or O; m=0-6 (e.g. 0, 1, 2, 3, 4, 5, or 6).

In this exemplary reaction, step (a) is conducted in the presence of N-bromosuccinimide (NBS), α,α'-Azoisobutyronitrile (AIBN), and $CCl_4$, at a temperature in the range of from about 45-75° C., for about 5 h. (e.g. from about 1-10, 2-9, 3-8, 4-8, or 5 or 6 hours); and step (b) is conducted in the presence of $K_2CO_3$ and anhydrous DMF, room temperature, for about 5-10 h.

A generic scheme for making the promoiety-containing compounds disclosed herein is depicted below in Scheme II:

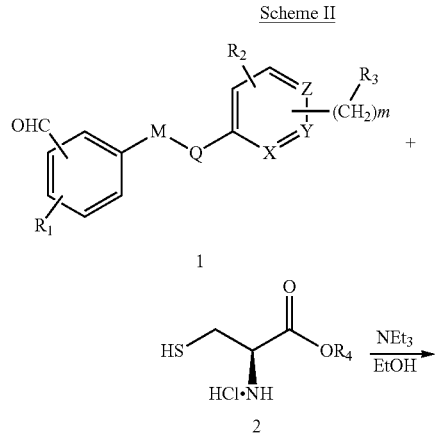

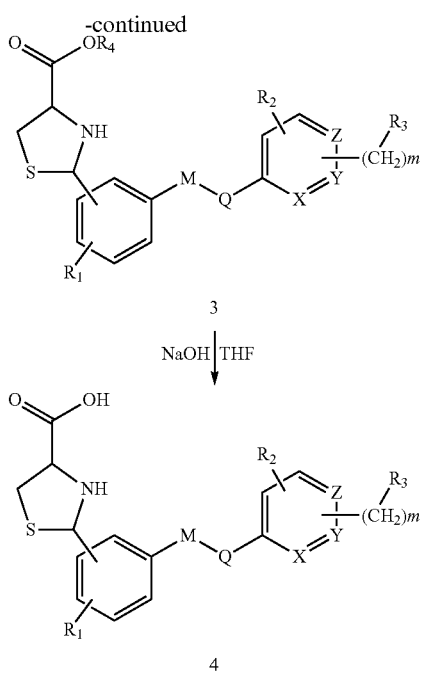

where R1 and R2 are the same or different and are H; hydroxyl; halogen; or substituted or unsubstituted: alkyl, alkoxy, aryl, O-aryl, cycloalkane or heterocycle; R3 is an alkyl ester, aryl ester, an alkylamide, an arylamide, phosphate or sulfate; R4 is linear or branched C1-C5 alkyl; M and Q are the same or different and are O or $(CH_2)n$, where n=0-6 (e.g. 0, 1, 2, 3, 4, 5, or 6); X, Y, Z, W and V are the same or different and are (independently) H, C, N, S or O; m=0-6 (e.g. 0, 1, 2, 3, 4, 5, or 6).

A typical synthesis will involve the condensation of the aldehydes, 2 with equimolar of L-cysteine ethyl ester, 2 in the presence of N-ethyldiisopropylamine hydrochloride (EDA) or triethyl amine ($NET_3$) to afford the ethyl ester prodrug, 3. Hydrolysis of the ethyl ester protecting group of 3 with sodium hydroxide will yield the acid prodrug, 4.

In some exemplary aspects, the compounds include the "PP" series of compounds and are made by the following synthetic Scheme III:

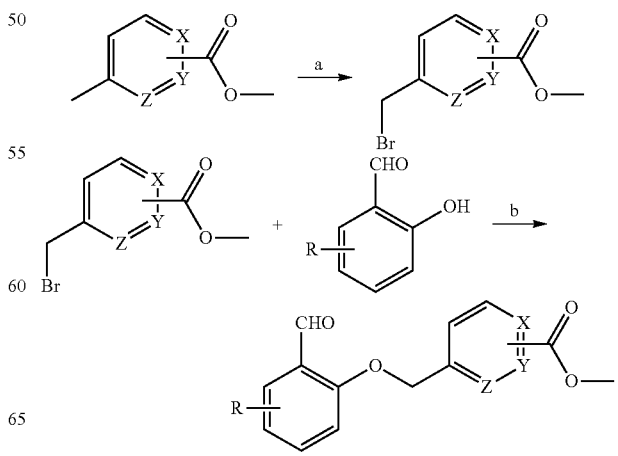

where X, Y and Z=C or N and R=—OCH$_3$ or —OH. In this exemplary reaction, step (a) is conducted in the presence of N-bromosuccinimide (NBS), α,α'-Azoisobutyronitrile (AIBN), and CCl$_4$, at a temperature in the range of from about 45-75° C., for about 5 h. (e.g. from about 1-10, 2-9, 3-8, 4-8, or 5 or 6 hours); and step (b) is conducted in the presence of K$_2$CO$_3$ and anhydrous DMF, room temperature, for about 5-10 h.

It is to be understood that this invention is not limited to particular embodiments described herein above and below, and as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

Example 1

We tested whether derivatizing the alcohol moiety of vanillin into aryl or alkyl amides and esters or inorganic phosphate esters would improve the pharmacologic properties of these compounds. First the substitutions would slow or make the compounds resistant to metabolism and lead to significantly sustained and enhanced pharmacologic activities. In addition, bulky ester or amide moieties would increase interactions with Hb with a concomitant increase in Hb oxygen affinity and lead to increased antisickling potency. The increased interactions would also slow down dissociation of the compound from the Hb and limit extensive metabolism of the free aromatic aldehyde. The increased hydrophobicity of the compound would also lead to increased partitioning of the compound into red blood cells and reduce off-target toxicity. Importantly, the bulky moiety on the pyridine ring would increase the interaction with the F helix subunit and lead to stereospecific inhibition of polymer formation, resulting in the compounds exhibiting a second antisickling mechanism of action that is independent of the primary mechanism of increasing Hb affinity for oxygen. The F helix is very important in stabilizing the polymer through secondary interaction between adjacent sickle Hb molecules, therefore any compound that binds to the F helix and affect its conformation is expected to abrogate this interaction and weaken the polymer with concomitant antisickling activity. Consistently, the Hb variant Stanleyville (αAsn78↔αLsy78) inhibits polymerization.[9]

Experimental Section

Chemical Synthesis

General information: All reagents used in the synthesis and functional assays were purchased from Sigma-Aldrich (St. Louis, Mo.) and Thermo Fisher Scientific (Waltham, Mass.) and utilized without additional purification. GBT440 was purchased from MedChemExpress, LLC (Monmouth Junction, N.J.). $^1$H-NMR and $^{13}$C-NMR spectra were obtained on a Bruker 400 MHz spectrometer and tetramethylsilane (TMS) was used as an internal standard. Peak positions are given in parts per million (δ). Column chromatography was performed on silica gel (grade 60 mesh; Bodman Industries, Aston, Pa.). Routine thin-layer chromatography (TLC) was performed on silica gel GHIF plates (250 vim, 2.5×10 cm; Analtech Inc., Newark, Del.). MS spectra were obtained from a Perkin Elmer Flexar™ UHPLC with AxION® 2 Time of Flight (TOF) Mass Spectrometer, and the molecular weight of the compounds was within 0.005% of calculated values. Infrared spectra were obtained on Thermo Scientific™ Nicolet™ iS10 FT-IR. Purity of the compounds was determined by HPLC using Varian Microsorb™ 100-5 C18 column (250×4.6 mm), using Prostar 325 UV-Vis (210 nm) as the detector. The HPC parameters used were: injection volume=15 μL. sample concentration=3 mM, mobile phase=60MeCN-40H$_2$O, flow rate=1 mL/min.

Statistical Analyses: All functional and biological assays evaluating antisickling properties, Hb modification and oxygen affinity changes were conducted in three biological replicates. Results are reported as mean values with standard deviations, from triplicate analyses.

Methyl 6-(bromomethyl)nicotinate

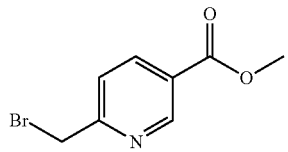

A mixture of methyl 6-methylnicotinate (1 eq) and α,α'-Azoisobutyronitrile (AIBN) (10%) was dissolved in carbontetrachloride (CCl₄). The solution was heated and N-bromosuccinimide (NBS) (1.1 eq) solution in CCl₄ was added drop wise and refluxed for 5 hours. The reaction was cooled to room temperature and the solvent evaporated. The mixture was then extracted using dichloromethane and water followed by washing the organic layer with brine. The organic layer was dried over sodium sulfate, filtered, evaporated and the crude product was purified using SiO₂ column chromatography and eluted with the solvent system EtOAc:hexanes=2:3 to obtain pure product as white powder and the yield was 66%. ¹H-NMR (400 MHz, DMSO-d₆): δ 9.16 (d, J=1.56 Hz, 1H), 8.30 (dd, J=8.12, 2.2 Hz, 1H), 7.53 (dd, J=8.12, 0.48 Hz, 1H), 4.58 (s, 2H), 3.96 (s, 3H). HRMS (ESI) m/z found 229.98 [M+H]⁺, Calculated 230.0586 [M]⁺.

Methyl 2-(bromomethyl)nicotinate

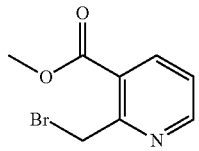

A mixture of methyl 2-methylnicotinate (1 eq) and α,α'-Azoisobutyronitrile (AIBN) (10%) was dissolved in carbontetrachloride (CCl₄). The solution was heated and N-bromosuccinimide (NBS) (1.1 eq) solution in CCl₄ was added drop wise and refluxed for 5 hours. The reaction was cooled to room temperature and the solvent evaporated. The mixture was then extracted using dichloromethane and water followed by washing the organic layer with brine. The organic layer was dried over sodium sulfate, filtered, evaporated and the crude product was purified using SiO₂ column chromatography and eluted with the solvent system EtOAc:hexanes=2:3 to obtain pure product as orange powder and the yield was 65%. ¹H-NMR (400 MHz, DMSO-d₆): δ 8.71 (dd, J=4.8, 1.76 Hz, 1H), 8.28 (dd, J=7.92, 1.76 Hz, 1H), 7.33 (m, 1H), 5.04 (s, 2H), 3.98 (s, 3H). HRMS (ESI) m/z found 229.98 [M+H]⁺, Calculated 230.0586 [M]⁺.

Methyl 6-(bromomethyl)picolinate

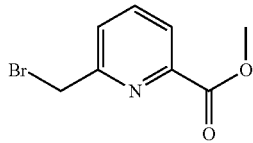

A mixture of methyl 6-methylpicolinate (1 eq) and α,α-Azoisobutyronitrile (AIBN) (10%) was dissolved in carbontetrachloride (CCl₄). The solution was heated and N-bromosuccinimide (NBS) (1.1 eq) solution in CCl₄ was added drop wise and refluxed for 5 hours. The reaction was cooled to room temperature and the solvent evaporated. The mixture was then extracted using dichloromethane and water followed by washing the organic layer with brine. The organic layer was dried over sodium sulfate, filtered, evaporated and the crude product was purified using SiO₂ column chromatography and eluted with the solvent system EtOAc:hexanes=2:3 to obtain pure product as white powder and the yield was 66%. ¹H-NMR (400 MHz, DMSO-d₆): δ 8.05 (d, J=7.68 Hz, 1H), 7.99 (t, J=7.72 Hz, 1H), 7.77 (d, J=7.68 Hz, 1H), 4.67 (s, 2H), 3.98 (s, 3H). HRMS (ESI) m/z found 229.98 [M+H]⁺, Calculated 230.0586 [M]⁺.

Methyl 2-methylisonicotinate

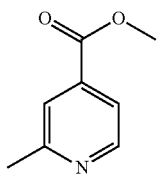

A few drops of concentrated sulphuric acid were added to a solution of methylisonicotinic acid in methanol. The mixture was refluxed for 48 hours. The resultant reaction mixture was neutralized with saturated sodium bicarbonate solution followed by extraction with ethyl acetate and water. The organic layer was dried over sodium sulfate, filtered and solvent evaporated. The crude product was purified using SiO₂ column chromatography and eluted with the solvent system EtOAc:hexanes=4:1. The pure compound was obtained as colorless oil with 96% yield. ¹H-NMR (400 MHz, DMSO-d₆): δ 8.66 (d, J=5.08 Hz, 1H), 7.71 (s, 1H), 7.63 (dd, J=5.04, 0.32 Hz, 1H), 3.89 (s, 2H), 2.56 (s, 3H). HRMS (ESI) m/z found 152.07 [M+H]⁺, Calculated 151.1626 [M]⁺.

Methyl 2-(bromomethyl)isonicotinate

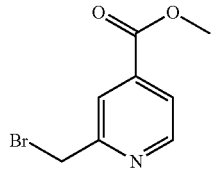

A mixture of methyl 2-methylisonicotinate (1 eq) and α,α'-Azoisobutyronitrile (AIBN) (10%) was dissolved in carbontetrachloride (CCl₄). The solution was heated and N-bromosuccinimide (NBS) (1.1 eq) solution in CCl₄ was added drop wise and refluxed for 5 hours. The reaction was cooled to room temperature and the solvent evaporated. The mixture was then extracted using dichloromethane and water followed by washing the organic layer with brine. The organic layer was dried over sodium sulfate, filtered, evaporated and the crude product was purified using SiO₂ column chromatography and eluted with the solvent system EtOAc:hexanes=2:3 to obtain pure product as dark blue colored powder and the yield was 66%. ¹H-NMR (400 MHz, DMSO-d₆): δ 8.77 (dd, J=5, 0.64 Hz, 1H), 8.02 (m, 1H), 7.77 (dd, J=5, 1.56 Hz, 1H), 4.81 (s, 2H), 3.91 (s, 3H). HRMS (ESI) m/z found 229.98 [M+H]⁺, Calculated 230.0586 [M]⁺.

Methyl 5-(bromomethyl)picolinate

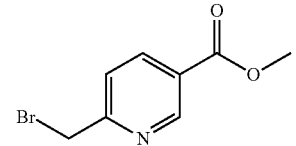

A mixture of methyl 2-methylisonicotinate (1 eq) and α,α'-Azoisobutyronitrile (AIBN) (10%) was dissolved in carbontetrachloride (CCl₄). The solution was heated at 48° C. and N-bromosuccinimide (NBS) (1.1 eq) solution in CCl₄ was added drop wise and stirred for 5 hours. The reaction was cooled to room temperature and the solvent evaporated. The mixture was then extracted using dichloromethane and water followed by washing the organic layer with brine. The organic layer was dried over sodium sulfate, filtered, evaporated and the crude product was purified using $SiO_2$ column chromatography and eluted with the solvent system EtOAc:hexanes=2:3 to obtain pure product as white powder and the yield was 66%. $^1$H-NMR (400 MHz, DMSO-$d_6$): δ 8.78 (t, J=1.48 Hz, 1H), 8.06 (d, J=1.36 Hz, 2H), 4.82 (s, 2H), 3.89 (s, 3H). HRMS (ESI) m/z found 229.98 [M+H]$^+$, Calculated 230.0586 [M]$^+$.

Methyl 6-((2-formyl-4-methoxyphenoxy)methyl)nicotinate (PP1)

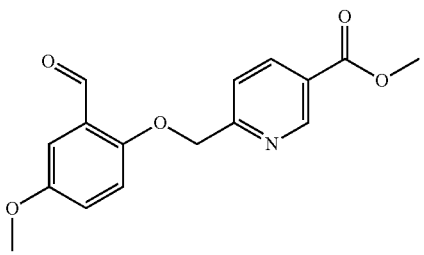 [SMILES: COC(=O)c1ccc(COc2ccc(OC)cc2C=O)nc1]

A mixture of 2-hydroxyl-5-methoxybenzaldehyde (1 eq) and methyl 6-(bromomethyl)nicotinate (1 eq) was dissolved in anhydrous N,N-Dimethylformamide (DMF). Anhydrous potassium carbonate ($K_2CO_3$) (1.2 eq) was added to this mixture and the reaction was stirred at room temperature for 8-10 hours. The solvent was then evaporated and the reaction mixture extracted with ethyl acetate and water. The organic layer was dried over sodium sulfate, filtered and the solvent evaporated. The crude product was purified using $SiO_2$ column chromatography and eluted with the solvent system EtOAc:hexanes=3:2 to obtain pure product as white powder with a yield of 82%. IR (Diamond, cm$^{-1}$): 2922, 2867, 1721, 1669, 1620, 1585, 1499, 1446, 1391, 1370, 1286, 1224, 1174, 1141, 1121; $^1$H-NMR (400 MHz, DMSO-$d_6$): δ 10.49 (s, 1H), 9.08 (m, 1H), 8.36 (dd, J=8.16, 2.16 Hz, 1H), 7.80 (d, J=8.12 Hz, 1H), 7.25 (m, 3H), 5.42 (s, 2H), 3.91 (s, 3H), 3.77 (s, 3H); $^{13}$C-NMR (100 MHz, DMSO-$d_6$): δ 188.94, 165.00, 161.04, 154.62, 153.62, 149.59, 137.82, 125.03, 124.77, 122.85, 121.31, 115.97, 110.78, 71.02, 55.59, 52.38. HRMS (ESI) m/z found 324.07 (M+Na)$^+$, Calculated 301.2940 [M]$^+$. The purity of the compound was checked by HPLC and was found to be 97% pure.

Methyl 2-((2-formyl-4-methoxyphenoxy)methyl)nicotinate (PP2)

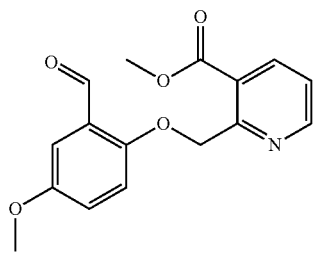 [SMILES: COC(=O)c1cccnc1COc1ccc(OC)cc1C=O]

A mixture of 2-hydroxyl-5-methoxybenzaldehyde (1 eq) and methyl 2-(bromomethyl)nicotinate (1 eq) was dissolved in anhydrous N,N-Dimethylformamide (DMF). Anhydrous potassium carbonate ($K_2CO_3$) (1.2 eq) was added to this mixture and the reaction was stirred at room temperature for 8-10 hours. The solvent was then evaporated and the reaction mixture was extracted with ethyl acetate and water. The organic layer was dried over sodium sulfate, filtered and the solvent evaporated. The crude product was purified using $SiO_2$ column chromatography and eluted with the solvent system EtOAc:hexanes=3:2 to obtain pure product as pale yellow powder with a yield of 82%. IR (Diamond, cm$^{-1}$): 2920, 1719, 1684, 1667, 1622, 1583, 1535, 1492, 1445, 1404, 1372, 1276, 1215, 1168, 1142; $^1$H-NMR (400 MHz, DMSO-$d_6$): δ 10.25 (s, 1H), 8.74 (dd, J=4.76, 1.48 Hz, 1H), 8.23 (dd, J=7.8, 1.44 Hz, 1H), 7.55 (m, 1H), 7.2 (m, 3H), 5.56 (s, 2H), 3.78 (s, 3H), 3.75 (s, 3H); $^{13}$C-NMR (100 MHz, DMSO-$d_6$): δ 188.73, 166.14, 155.39, 155.29, 153.46, 151.55, 138.47, 126.17, 124.86, 123.66, 122.98, 116.13, 110.06, 70.98, 55.61, 52.54. HRMS (ESI) m/z found 302.11 (M+H)$^+$, 324.09 (M+Na)$^+$, Calculated 301.2940 [M]$^+$. The purity of the compound was checked by HPLC and was found to be 99% pure.

Methyl 6-((2-formyl-4-methoxyphenoxy)methyl)picolinate (PP3)

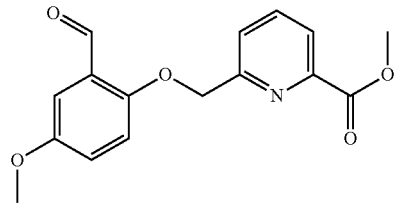 [SMILES: COC(=O)c1cccc(COc2ccc(OC)cc2C=O)n1]

A mixture of 2-hydroxyl-5-methoxybenzaldehyde (1 eq) and methyl 6-(bromomethyl)picolinate (1 eq) was dissolved in anhydrous N,N-Dimethylformamide (DMF). Anhydrous potassium carbonate ($K_2CO_3$) (1.2 eq) was added to this mixture and the reaction was stirred at room temperature for 8-10 hours. The solvent was then evaporated and the reaction mixture extracted with ethyl acetate and water. The organic layer was dried over sodium sulfate, filtered and the solvent evaporated. The crude product was purified using $SiO_2$ column chromatography and eluted with the solvent system EtOAc:hexanes=3:2 to obtain pure product as white powder with a yield of 82%. IR (Diamond, cm$^{-1}$): 2953, 2851, 1720, 1682, 1618, 1585, 1494, 1396, 1369, 1296, 1222, 1169, 1141; $^1$H-NMR (400 MHz, DMSO-$d_6$): δ 10.47 (s, 1H), 8.03 (m, 2H), 7.87 (d, J=7.32 Hz, 1H), 7.26 (m, 3H), 5.38 (s, 2H), 3.90 (s, 3H), 3.76 (s, 3H); $^{13}$C-NMR (100 MHz, DMSO-$d_6$): δ 189.03, 164.99, 156.95, 154.68, 153.59, 146.99, 138.57, 125.05, 125.01, 123.95, 123.84, 115.99, 110.76, 71.08, 55.59, 52.39. HRMS (ESI) m/z found 302.10 (M+H)$^+$, 324.08 (M+Na)$^+$, Calculated 301.2940 [M]$^+$. The purity of the compound was checked by HPLC and was found to be 98% pure.

Methyl 2-((2-formyl-4-methoxyphenoxy)methyl)isonicotinate (PP4)

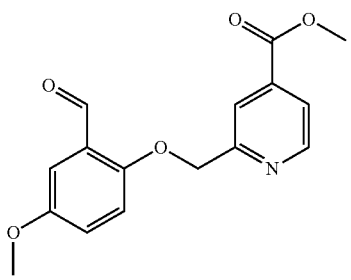 [SMILES: COC(=O)c1ccnc(COc2ccc(OC)cc2C=O)c1]

A mixture of 2-hydroxyl-5-methoxybenzaldehyde (1 eq) and methyl 2-(bromomethyl)isonicotinate (1 eq) was dissolved in anhydrous N,N-Dimethylformamide (DMF). Anhydrous potassium carbonate ($K_2CO_3$) (1.2 eq) was added to this mixture and the reaction was stirred at room temperature for 8-10 hours. The solvent was then evaporated and the reaction mixture extracted with ethyl acetate and water. The organic layer was dried over sodium sulfate, filtered and the solvent evaporated. The crude product was purified using Si& column chromatography and eluted with the solvent system EtOAc:hexanes=3:2 to obtain pure product as white powder with a yield of 82%. IR (Diamond, $cm^{-1}$): 2923, 1729, 1686, 1608, 1566, 1450, 1382, 1292, 1276, 1216, 1190, 1171; $^1$H-NMR (400 MHz, DMSO-$d_6$): δ 10.43 (s, 1H), 8.81 (dd, J=5, 0.56 Hz, 1H), 8.02 (s, J=1.44 Hz, 1H), 7.80 (dd, J=5.04, 1.56 Hz, 1H), 7.24 (m, 3H), 5.41 (s, 2H), 3.91 (s, 3H), 3.76 (s, 3H); $^{13}$C-NMR (100 MHz, DMSO-$d_6$): δ 188.81, 165.02, 157.80, 154.78, 153.63, 150.44, 137.79, 125.09, 122.92, 121.82, 120.33, 116.25, 110.73, 71.27, 55.58, 52.81. HRMS (ESI) m/z found 302.10 $(M+H)^+$, 324.08 $(M+Na)^+$, Calculated 301.2940 $[M]^+$. The purity of the compound was checked by HPLC and was found to be 98% pure.

Methyl 6-((2-formyl-3-hydroxyphenoxy)methyl)nicotinate (PP5)

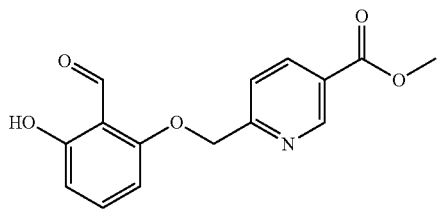 [SMILES: COC(=O)c1ccc(COc2cccc(O)c2C=O)nc1]

A mixture of 2,6-dihydroxybenzaldehyde (1 eq) and methyl 6-(bromomethyl)nicotinate (1 eq) was dissolved in anhydrous N,N-Dimethylformamide (DMF). Anhydrous potassium carbonate ($K_2CO_3$) (1.24 was added to this mixture and the reaction was stirred at room temperature for 4 hours. The solvent was then evaporated and the reaction mixture extracted with ethyl acetate and water. The organic layer was dried over sodium sulfate, filtered and the solvent evaporated. The crude product was purified using $SiO_2$ column chromatography and eluted with the solvent system EtOAc:hexanes=6:1 to obtain pure product as white powder with a yield of 58%. IR (Diamond, $cm^{-1}$): 3299, 2959, 1726, 1694, 1620, 1458, 1437, 1382, 1343, 1285, 1233, 1172, 1122; $^1$H-NMR (400 MHz, DMSO-$d_6$): δ 11.73 (s, 1H), 10.45 (s, 1H), 9.09 (s, 1H), 8.34 (d, J=8.12, 1H), 7.81 (d, J=8.28 Hz, 1H), 7.51 (t, J=8.4 Hz, 1H), 6.67 (d, J=8.52 Hz, 1H), 6.56 (d, J=8.36 Hz) 5.41 (s, 2H), 3.90 (s, 3H); $^{13}$C-NMR (100 MHz, DMSO-$d_6$): δ 193.85, 165.39, 163.86, 160.84, 160.41, 150.66, 138.40, 138.12, 125.47, 120.52, 111.05, 110.86, 102.24, 70.91, 52.47. HRMS (ESI) m/z found 288.08 $(M+H)^+$, 310.08 $(M+Na)^+$, Calculated 301.2940 [M]. The purity of the compound was checked by HPLC and was found to be 100% pure.

Methyl 2-((2-formyl-3-hydroxyphenoxy)methyl)nicotinate (PP6)

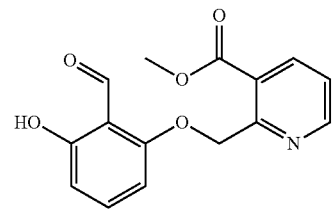 [SMILES: COC(=O)c1cccnc1COc1cccc(O)c1C=O]

A mixture of 2,6-dihydroxybenzaldehyde (1 eq) and methyl 2-(bromomethyl)nicotinate (1 eq) was dissolved in anhydrous N,N-Dimethylformamide (DMF). Anhydrous potassium carbonate ($K_2CO_3$) (1.2 eq) was added to this mixture and the reaction was stirred at room temperature for 4 hours. The solvent was then evaporated and the reaction mixture was extracted with ethyl acetate and water. The organic layer was dried over sodium sulfate, filtered and the solvent evaporated. The crude product was purified using $SiO_2$ column chromatography and eluted with the solvent system EtOAc:hexanes=5:2 to obtain pure product as pale yellow powder with a yield of 58%. IR (Diamond, $cm^{-1}$): 2956, 1713, 1618, 1637, 1571, 1459, 1435, 1396, 1370, 1287, 1238, 1170, 1141; $^1$H-NMR (400 MHz, DMSO-$d_6$): δ 11.67 (s, 1H), 10.19 (s, 1H), 8.75 (dd, J=4.8, 1.68 Hz, 1H), 8.25 (dd, J=7.84, 1.68 Hz, 1H), 7.55 (m, 2H), 6.66 (d, J=8.2 Hz, 1H), 6.53 (d, J=8.4 Hz, 1H), 5.58 (s, 2H), 3.79 (s, 3H); $^{13}$C-NMR (100 MHz, DMSO-$d_6$): δ 193.68, 166.15, 162.26, 161.44, 155.02, 151.73, 138.75, 138.31, 126.02, 123.60, 110.66, 109.49, 103.51, 70.59, 52.50. MS (ESI) m/z found 288.09 $(M+H)^+$, 310.07 $(M+Na)^+$, Calculated 301.2940 [M]. The purity of the compound was checked by HPLC and was found to be 100% pure.

Methyl 2-((2-formyl-3-hydroxyphenoxy)methyl)isonicotinate (PP7)

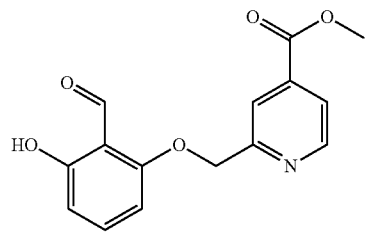 [SMILES: COC(=O)c1ccnc(COc2cccc(O)c2C=O)c1]

A mixture of 2,6-dihydroxybenzaldehyde (1 eq) and methyl 2-(bromomethyl)isonicotinate (1 eq) was dissolved in anhydrous N,N-Dimethylformamide (DMF). Anhydrous potassium carbonate ($K_2CO_3$) (1.2 eq) was added to this mixture and the reaction was stirred at room temperature for 4 hours. The solvent was then evaporated and the reaction mixture extracted with ethyl acetate and water. The organic layer was dried over sodium sulfate, filtered and the solvent evaporated. The crude product was purified using $SiO_2$ column chromatography and eluted with the solvent system EtOAc:hexanes=5:2 to obtain pure product as pale yellow powder with a yield of 58%. IR (Diamond, cm$^{-1}$): 2961, 1733, 1716, 1639, 1620, 1577, 1460, 1441, 1373, 1342, 1293, 1235, 1215, 1174; $^1$H-NMR (400 MHz, DMSO-$d_6$): δ 11.68 (s, 1H), 10.39 (s, 1H), 8.81 (dd, J=5, 0.6 Hz, 1H), 8.03 (d, J=0.56 Hz, 1H), 7.81 (dd, J=5, 1.56 Hz 1H), 7.51 (t, J=8.4 Hz, 1H), 5.41 (s, 2H), 3.91 (s, 3H); $^{13}$C-NMR (100 MHz, DMSO-$d_6$): δ 193.51, 165.02, 162.37, 160.80, 157.43, 150.43, 138.66, 137.84, 121.89, 120.38, 110.83, 109.74, 103.56, 70.69, 52.83. MS (ESI) m/z found 288.09 (M+H)$^+$, 310.07 (M+Na)$^+$, Calculated 301.2940 [M]$^+$. The purity of the compound was checked by HPLC and was found to be 99% pure.

Methyl
3-((2-formyl-4-methoxyphenoxy)methyl)picolinate
(PP8)

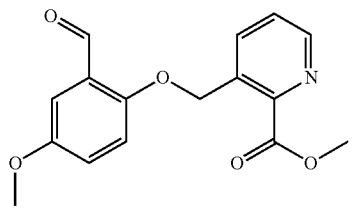 [SMILES: COC(=O)c1ncccc1COc1ccc(OC)cc1C=O]

A mixture of 2-hydroxyl-5-methoxybenzaldehyde (1 eq) and methyl 3-(bromomethyl)picolinate (1 eq) was dissolved in anhydrous N,N-Dimethylformamide (DMF). Anhydrous potassium carbonate ($K_2CO_3$) (1.2 eq) was added to this mixture and the reaction was stirred at room temperature for 8-10 hours. The solvent was then evaporated and the reaction mixture extracted with ethyl acetate and water. The organic layer was dried over sodium sulfate, filtered and the solvent evaporated. The crude product was purified using $SiO_2$ column chromatography and eluted with the solvent system EtOAc:hexanes 3:2 to obtain pure product as pale yellow powder with a yield of 82%. IR (Diamond, cm$^{-1}$): 2897, 1712, 1671, 1607, 1567, 1490, 1445, 1398, 1365, 1275, 1232, 1165, 1139, 1106; $^1$H-NMR (400 MHz, DMSO-$d_6$): δ 10.35 (s, 1H), 8.65 (dd, J=4.6, 1.28 Hz, 1H), 8.2 (dd, J=7.84, 0.76 Hz, 1H), 7.66 (dd, J=7.88, 4.68 Hz, 1H), 7.24 (m, 3H), 5.49 (s, 2H), 3.83 (s, 3H), 3.77 (s, 3H); $^{13}$C-NMR (100 MHz, DMSO-$d_6$): δ 188.81, 166.12, 154.66, 153.55, 148.43, 146.69, 136.89, 133.04, 126.43, 124.89, 122.96, 115.79, 110.68, 67.44, 55.56, 52.34. MS (ESI) m/z found 324.08 (M+Na)$^+$, Calculated 301.2940 [M]$^+$. The purity of the compound was checked by HPLC and was found to be 98% pure.

Methyl
5-((2-formyl-4-methoxyphenoxy)methylpicolinate
(PP9)

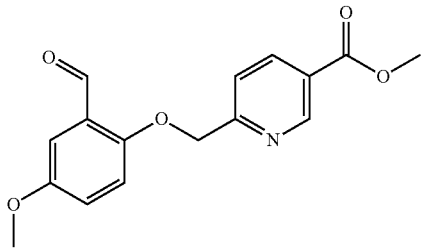 [SMILES: COC(=O)c1ccc(COc2ccc(OC)cc2C=O)nc1]

A mixture of 2-hydroxyl-5-methoxybenzaldehyde (1 eq) and methyl 5-(bromomethyl)picolinate (1 eq) was dissolved in anhydrous N,N-Dimethylformamide (DMF). Anhydrous potassium carbonate ($K_2CO_3$) (1.2 eq) was added to this mixture and the reaction was stirred at room temperature for 8-10 hours. The solvent was then evaporated and the reaction mixture extracted with ethyl acetate and water. The organic layer was dried over sodium sulfate, filtered and the solvent evaporated. The crude product was purified using $SiO_2$ column chromatography and eluted with the solvent system EtOAc:hexanes 3:2 to obtain pure product as white powder with a yield of 82%. IR (Diamond, cm$^{-1}$): 2962, 2864, 2767, 1719, 1684, 1673, 1588, 1489, 1458, 1395, 1355, 1274, 1218, 1198, 1150, 1127; $^1$H-NMR (400 MHz, DMSO-$d_6$): δ 10.40 (s, 1H), 8.84 (d, J=1.36 Hz, 1H), 8.10 (m, 2H), 7.28 (m, 2H), 7.2 (d, J=2.92 Hz, 1H), 5.39 (s, 2H), 3.89 (s, 3H), 3.76 (s, 3H); $^{13}$C-NMR (100 MHz, DMSO-$d_6$): δ 188.77, 154.89, 154.57, 148.62, 135.93, 135.67, 135.93, 135.67, 125.92, 125.17, 123.28, 114.92, 111.30, 68.52, 55.90, 52.97. MS (ESI) m/z found 302.10 (M+H)$^+$, 324.09 (M+Na)$^+$, Calculated 301.2940 [M]$^+$. The purity of the compound was checked by HPLC and was found to be 98% pure.

Methyl
6-((2-formyl-3-hydroxyphenoxy)methyl)picolinate
(PP10)

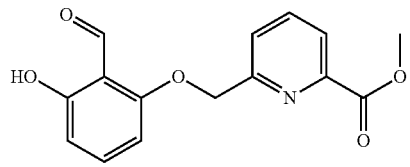 [SMILES: COC(=O)c1cccc(COc2cccc(O)c2C=O)n1]

A mixture of 2,6-dihydroxybenzaldehyde (1 eq) and methyl 6-(bromomethyl)picolinate (1 eq) was dissolved in anhydrous N,N-Dimethylformamide (DMF). Anhydrous potassium carbonate ($K_2CO_3$) (1.2 eq) was added to this mixture and the reaction was stirred at room temperature for 4 hours. The solvent was then evaporated and the reaction mixture extracted with ethyl acetate and water. The organic layer was dried over sodium sulfate, filtered and the solvent evaporated. The crude product was purified using $SiO_2$ column chromatography and eluted with the solvent system EtOAc:hexanes=6:1 to obtain pure product as white powder with a yield of 58%. IR (Diamond, cm$^{-1}$): 3065, 3010, 2956, 2890, 1738, 1697, 1640, 1614, 1583, 1462, 1454, 1400, 1358, 1297, 1242, 1190, 1171, 1150; $^1$H-NMR (400 MHz, DMSO-d$_6$): δ 11.74 (s, 1H), 10.44 (s, 1H), 8.04 (m, 2H), 7.91 (dd, J=7.48, 1.12 Hz, 1H), 7.52 (t, J=8.4 Hz, 1H), 6.7 (d, J=8 Hz, 1H), 6.56 (d, J=8.4 Hz, 1H), 5.39 (s, 2H), 3.90 (s, 3H); $^{13}$C-NMR (100 MHz, DMSO-d$_6$): δ 193.79, 164.99, 162.43, 160.69, 160.62, 149.59, 138.65, 137.84, 124.81, 121.26, 110.79, 109.81, 103.42, 70.49, 52.41. MS (ESI) m/z found 288.09 (M+H)$^+$, 310.07 (M+Na)$^+$, Calculated 301.2940 [M]$^+$. The purity of the compound was checked by HPLC and was found to be 100% pure.

Methyl
3-((2-formyl-3-hydroxyphenoxy)methyl)picolinate
(PP11)

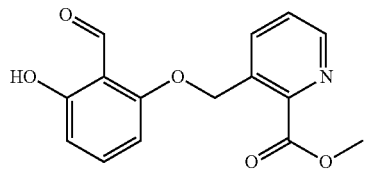 [SMILES: COC(=O)c1ncccc1COc1cccc(O)c1C=O]

A mixture of 2,6-dihydroxybenzaldehyde (1 eq) and methyl 3-(bromomethyl)picolinate (1 eq) was dissolved in anhydrous N,N-Dimethylformamide (DMF). Anhydrous potassium carbonate (K$_2$CO$_3$) (1.2 eq) was added to this mixture and the reaction was stirred at room temperature for 4 hours. The solvent was then evaporated and the reaction mixture extracted with ethyl acetate and water. The organic layer was dried over sodium sulfate, filtered and the solvent evaporated. The crude product was purified using SiO$_2$ column chromatography and eluted with the solvent system EtOAc:hexanes=6:1 to obtain pure product as pale yellow powder with a yield of 54%. IR (Diamond, cm$^{-1}$): 3092, 2923, 2851, 1774, 1712, 1632, 1599, 1566, 1515, 1478, 1366, 1276, 1231, 1180, 1136, 1072; $^1$H-NMR (400 MHz, DMSO-d$_6$): δ 11.72 (s, 1H), 10.32 (s, 1H), 8.65 (dd, J=4.64, 1.52 Hz, 1H), 8.22 (m, 1H), 7.66 (dd, J=7.88, 4.64 Hz, 1H), 7.54 (t, J=8.4 Hz, 1H), 6.66 (d, J=8 Hz, 1H), 6.57 (d, J=8.4 Hz, 1H), 5.51 (s, 2H), 3.84 (s, 3H), $^{13}$C-NMR (100 MHz, DMSO-d$_6$): δ 193.59, 166.09, 162.46, 160.68, 148.53, 146.54, 138.72, 136.83, 132.78, 126.44, 110.74, 109.79, 103.26, 67.04, 52.35. MS (ESI) m/z found 310.08 (M+Na)$^+$, Calculated 301.2940 [M]$^+$. The purity of the compound was checked by HPLC and was found to be 100% pure.

Methyl
5-((2-formyl-4-methoxyphenoxy)methyl)nicotinate
(PP12)

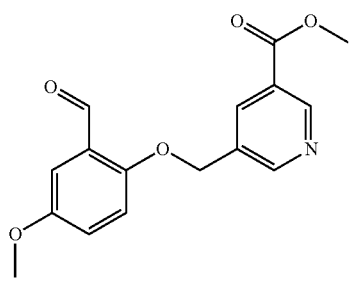 [SMILES: COC(=O)c1cncc(COc2ccc(OC)cc2C=O)c1]

A mixture of 2-hydroxyl-5-methoxybenzaldehyde (1 eq) and methyl 5-(bromomethyl)nicotinate (1 eq) was dissolved in anhydrous N,N-Dimethylformamide (DMF). Anhydrous potassium carbonate (K$_2$CO$_3$) (1.2 eq) was added to this mixture and the reaction was refluxed at room temperature for 8-10 hours. The solvent was then evaporated and the reaction mixture extracted with ethyl acetate and water. The organic layer was dried over sodium sulfate, filtered and the solvent evaporated. The crude product was purified using SiO$_2$ column chromatography and eluted with the solvent system EtOAc:hexanes=3:2 to obtain pure product as white powder with a yield of 82%. IR (Diamond, cm$^{-1}$): 2969, 1718, 1670, 1602, 1572, 1498, 1435, 1405, 1382, 1279, 1217, 1185, 1160, 1119; $^1$H-NMR (400 MHz, DMSO-d$_6$): δ 10.37 (s, 1H), 9.06 (d, J=2 Hz, 1H), 8.97 (d, J=2.04 Hz, 1H), 8.42 (t, J=2.04 Hz, 1H), 7.29 (m, 2H), 7.2 (d, J=3.08 Hz, 1H), 5.38 (s, 2H), 3.9 (s, 3H), 3.77 (s, 3H); $^{13}$C-NMR (100 MHz, DMSO-d$_6$): δ 188.87, 165.04, 154.64, 153.64, 152.90, 149.49, 135.99, 132.63, 125.44, 125.13, 122.88, 116.21, 110.71, 67.83, 55.58, 52.49. MS (ESI) m/z found 324.08 (M+Na)$^+$, Calculated 301.2940 [M]$^+$. The purity of the compound was checked by HPLC and was found to be 99% pure.

Methyl
5-((2-formyl-3-hydroxyphenoxy)methyl)nicotinate
(PP13)

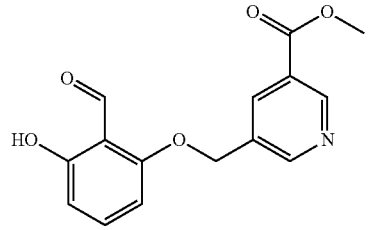 [SMILES: COC(=O)c1cncc(COc2cccc(O)c2C=O)c1]

A mixture of 2,6-dihydroxybenzaldehyde (1 eq) and methyl 5-(bromomethyl)nicotinate (1 eq) was dissolved in anhydrous N,N-Dimethylformamide (DMF). Anhydrous potassium carbonate (K$_2$CO$_3$) (1.2 eq) was added to this mixture and the reaction was stirred at room temperature for 4 hours. The solvent was then evaporated and the reaction mixture extracted with ethyl acetate and water. The organic layer was dried over sodium sulfate, filtered and the solvent evaporated. The crude product was purified using SiO$_2$ column chromatography and eluted with the solvent system EtOAc:hexanes=6:1 to obtain pure product as white powder with a yield of 54%. IR (Diamond, cm$^{-1}$): 2907, 1719, 1643, 1617, 1584, 1460, 1429, 1397, 1370, 1292, 1246, 1179, 1152, 1121; $^1$H-NMR (400 MHz, DMSO-d$_6$): δ 11.72 (s, 1H), 10.33 (s, 1H), 9.05 (d, J=1.8 Hz, 1H), 8.99 (d, J=1.76 Hz, 1H), 8.43 (t, J=2 Hz, 1H), 7.55 (t, J=8.2 Hz, 1H), 6.73 (d, J=8.2 Hz, 1H), 6.56 (d, J=8.44 Hz, 1H), 5.39 (s, 2H), 3.91 (s, 3H); $^{13}$C-NMR (100 MHz, DMSO-d$_6$): δ 193.74, 176.82, 165.04, 162.40, 160.72, 152.87, 149.53, 138.63, 135.99, 132.32, 110.80, 109.76, 103.42, 67.28, 52.49. MS (ESI) m/z found 288.08 (M+H)$^+$, Calculated 301.2940 [M]$^+$. The purity of the compound was checked by HPLC and was found to be 99% pure.

Methyl 5-((2-formyl-3-hydroxyphenoxy)methyl)picolinate (PP14)

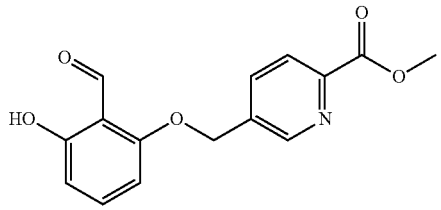

A mixture of 2,6-dihydroxybenzaldehyde (1 eq) and methyl 5-(bromomethyl)picolinate (1 eq) was dissolved in anhydrous N,N-Dimethylformamide (DMF). Anhydrous potassium carbonate ($K_2CO_3$) (1.2 eq) was added to this mixture and the reaction was stirred at room temperature for 4 hours. The solvent was then evaporated and the reaction mixture extracted with ethyl acetate and water. The organic layer was dried over sodium sulfate, filtered and the solvent evaporated. The crude product was purified using $SiO_2$ column chromatography and eluted with the solvent system EtOAc:hexanes=6:1 to obtain pure product as white powder with a yield of 54%. IR (Diamond, $cm^{-1}$): 2954, 1731, 1679, 1644, 1618, 1574, 1458, 1440, 1392, 1357, 1289, 1249, 1177, 1144, 1122; $^1$H-NMR (400 MHz, DMSO-$d_6$): δ 11.74 (s, 1H), 10.37 (s, 1H), 8.86 (s, 1H), 8.12 (m, 2H), 7.54 (t, J=8.4 Hz, 1H), 6.72 (d, J=8.32 Hz, 1H), 6.56 (d, J=8.4 Hz, 1H), 5.40 (s, 2H), 3.89 (s, 3H); $^{13}$C-NMR (100 MHz, DMSO-$d_6$): δ 193.83, 162.42, 160.69, 148.72, 147.01, 138.64, 136.32, 135.91, 135.78, 124.64, 109.79, 103.37, 67.31, 52.39. MS (ESI) m/z found 310.08 (M+Na)$^+$, Calculated 301.2940 [M]$^+$. The purity of the compound was checked by HPLC and was found to be 99% pure.

Blood Collection and Purification of Hemoglobin

Human blood samples were obtained from healthy volunteers at Virginia Commonwealth University. The use of the biological samples was reviewed and approved by the IRB, in accordance of institutional regulations. Leftover blood samples from patients with homozygous SS were obtained and utilized, based on an approved IRB protocol at the Children's Hospital of Philadelphia, with informed consent. Hemoglobin was purified from normal human blood samples according to the literature procedure.[10]

Oxygen Equilibrium Curve Studies

Oxygen equilibrium curve (OEC) studies to determine the effect of the compounds on Hb affinity for oxygen were conducted following standard procedure.[8,11] Whole blood (30% hematocrit) was incubated in the absence or presence of compounds (0.5 mM, 1.0 mM and 2.0 mM) solubilized in DMSO. The blood-compound reaction samples were then incubated in an IL 237 tonometer (Instrumentation Laboratories, Inc., Lexington, Mass.) for about 7 min at 37° C. under a gas mixture containing $O_2$ at concentrations of 0.804%, 2.935% and 5.528% and allowed to equilibrate at $O_2$ tensions of 6, 20 and 40 mmHg. After equilibration, the sample was removed via syringe and aspirated into an ABL 700 series table top automated blood gas analyzer (Radiometer America, Inc., Westlake, Ohio) to determine total hemoglobin (tHb), hematocrit (Hct), pH, $pCO_2$, partial pressure of oxygen ($pO_2$), and the Hb-$O_2$ saturation ($sO_2$) values. The measured values of $pO_2$ and $SO_2$ at each oxygen saturation level were then subjected to nonlinear regression analysis using the software Scientist (Micromath, Salt Lake City Utah) with the following equation:

$$sO_2\ \% = 100 \times \frac{pO_2^N\ \text{mmHg}}{P_{50}^N(\text{mmHg}) + pO_2^N(\text{mmHg})}$$

This equation was used to calculate $P_{50}$ and Hill coefficient (N) values. $\Delta P_{50}(\%)$ was determined as:

$$\Delta P_{50}(\%) = 100 \times \frac{P_{50}\ \text{in the absence of compound} - P_{50}\ \text{in the presence of compound}}{P_{50}\ \text{in the absence of compound}}$$

Adduct Formation Studies Using Normal Whole Blood and Hemoglobin

Time dependent and concentration dependent Hb-compound adduct formation studies were performed with whole blood using standard procedures. In a 96-well deep well plate (Thermo Scientific), 0.5 mM, 1.0 mM and 2.0 mM concentrations of the compounds were added to 600 μL of whole blood (30% hematocrit) and/or Hb (1.56 mM). These were incubated at 37° C. for 24 h with shaking (at 140 rpm). At 1, 4, 8, 12 and 24 h time intervals, 50 μL aliquots of this mixture were removed from each well using a multichannel pipette and added to respective tubes containing 50 μL of sodium cyanoborohydride (NaBH$_3$CN) and sodium borohydride (NaBH$_4$) mixture (1:1 v/v 50 mM stock) to terminate the Schiff-base reaction, fix the Schiff-base adducts and reduce the free reactive aldehyde.[12] After mixing, the tubes were stored immediately at −80° C. until ready for batch analysis by cation-exchange HPLC (Hitachi D-700 Series, Hitachi Instruments, Inc. San Jose, Calif.).[5,6] The observed Hb adducts, calculated as percentages (%) of Hb modification were plotted as a function of time (h); peak areas were quantitated using the HPLC software.

Hemoglobin Modification, Oxygen Equilibrium and Anti-sickling Studies Using Human Sickle Blood Blood suspensions from subjects with homozygous SCD (resuspended in Hemox™ buffer to a final hematocrit 20%) were incubated under air in the absence or presence of the compounds (0.5 mM, 1 mM and 2 mM) at 37° C. for 1 h to ensure that binding had attained equilibrium. The suspensions were then incubated under hypoxic conditions (2.5% oxygen/97.5% nitrogen) at 37° C. for 1 h. Aliquot samples were fixed with 2% glutaraldehyde solution without exposure to air, and then subjected to microscopic morphological analysis of bright field images (at 40× magnification) of single layer cells on an Olympus BX40 microscope fitted with an Infinity Lite B camera (Olympus), and the coupled Image Capture software. The residual samples were washed in phosphate-buffer saline, and hemolyzed in hypotonic lysis buffer for subsequent Hb-modification and oxygen equilibrium analyses.[8,12]

For oxygen equilibrium studies, approximately 100 μL aliquot samples from the above clarified lysate were added to 4 mL of 0.1M potassium phosphate buffer, pH 7.0, in cuvettes and subjected to hemoximetry analysis using a Hemox™ Analyzer (TCS Scientific Corp.) to assess $P_{50}$ shifts. Degree of $P_{50}$ shift (APO was expressed as percentage fractions of control DMSO-treated samples.

$$\Delta P_{50}(\%) = 100 \times \frac{P_{50} \text{ of lysates from untreated cells} - P_{50} \text{ of lysates from treated cells}}{P_{50} \text{ of lysates from unrteated cells}}$$

Finally, for the Hb adduct formation studies, the above clarified lysates were subjected to cation-exchange HPLC (Hitachi D-7000 Series, Hitachi Instruments, Inc., San Jose, Calif.), using a weak cation-exchange column (Poly CAT A: 30 mm×4.6 mm, Poly LC, Inc., Columbia, Md.). A commercial standard consisting of approximately equal amounts of composite HbF, HbA, HbS and HbC (Helena Laboratories, Beaumont, Tex.), was utilized as the reference for isotypes. The areas of new peaks, representing HbS adducts, were obtained, calculated as percentage fractions of total Hb area, and reported as levels of modified Hb.

Antisickling Activities of Compounds Under 100% Nitrogen

To demonstrate potential non Hb-$O_2$ affinity-dependent activities of the molecules, we tested the antisickling properties of selected compounds (PP9 and PP14) under complete deoxygenated conditions. We used TD7 and GBT440 as reference controls; the latter is also an aromatic aldehyde with the most potent reported in vitro p50 shifts and anti-sickling properties, and is currently in phase III clinical studies for the treatment of SCD. Briefly, antisickling studies were conducted as previously described, using 2 mM concentrations of the test molecules. After 1 h, aliquot samples were fixed with 2% glutaraldehyde without exposure to air. Then the incubation chamber was opened and exposed to air for 15 minutes to ensure complete re-oxygenation and reversal of the sickled cells to normal round cells. Reversal was confirmed by microscopy. The incubation chamber was then closed and the assay was repeated under 100% nitrogen gas for 30 minutes, at which point aliquots were obtained and fixed. Aliquot samples were then subjected to microscopic morphological analysis of bright field images (at 40× magnification) of single layer cells on an Olympus BX40 microscope fitted with an Infinity Lite B camera (Olympus), and the coupled Image Capture software. Resulting sickled cells (percentages) were compared across samples, and between aliquots of the same samples that had been obtained either under 2.5% oxygen or 100% nitrogen. This experimental design utilized aliquots of the same samples under different gas conditions, and thereby ensured that the assay was free of any potential errors associated with variability in hematocrit and accuracy in adding the molecules.

X-Ray Crystallography

Freshly made solutions of compounds in DMSO were added to deoxygenated (deoxy) Hb (30 mg/mL protein) at an Hb tetramer-compound ratio of 1:10. Then, the complex mixture was saturated with carbon monoxide and allowed to incubate for 2 h to form COHb-compound complexes. Sodium cyanoborohydride ($NaBH_3CN$) was then added to this mixture to reduce the Schiff-base adduct formed between the protein and compound to the corresponding irreversible alkylamine covalent bond. The resulting solution was crystalized using 10-20% PEG 6000, 100 mM HEPES buffer, pH 7.4 using the batch method as previously published.[12] Single cherry red needle crystals were formed in 1-3 days and were used to collect x-ray diffraction data at 100 K using Rigaku MicroMax™ 007HF X-ray Generator, Eiger R 4M Detector and Oxford Cobra Cryo-system (The Woodlands, Tex.). The crystals were first cryoprotected with 80 μL mother liquor mixed with 62 μL of 50% PEG6000. The dataset was processed with the d*trek software (Rigaku) and the CCP4 suite of programs.[13] The crystal structures of the COHb-compound complexes were determined by a molecular replacement method with Phenix program,[14] using the native R2-state crystal structure (PDB ID 1 BBB) as a search model. The structures were refined using both Phenix and CNS while model building and correction was carried out using COOT.[15,16]

In Vivo Pharmacologic Effect of PP Compounds in Mice

We tested in vivo pharmacologic (pharmacodynamics) effects of select PP compounds in C57BL/6 mice. The animals were treated with a single intraperitoneal (IP) (150 mg/kg body weight) dose of PP6, PP10, PP14, and TD7, which were formulated with 30% PEG300. Blood samples were obtained prior to treatment (0) and 1, 3 and 6 h post-treatment, via submandibular bleeding, and subjected to hemolysis using standard methods. Clarified lysates, free of cell debris and red blood cell ghosts were analyzed by cation-exchange HPLC to determine the levels of drug-modified hemoglobin (adducts); and to conduct oxygen equilibrium studies to determine degrees of shift in p50 values using methodologies described earlier for in vitro studies on human samples.[8,12]

In a subsequent follow-up experiment, a new excipient obtained from Catalent Pharma Solutions was also used to formulate PP14 and used for a single intraperitoneal (IP) and oral (150 mg/kg body weight) dose. Blood samples were obtained prior to treatment (0) and 1, 3 or 5 h post-treatment, via submandibular bleeding, and used to determine the levels of drug-modified hemoglobin (adducts); and to conduct oxygen equilibrium studies to determine degrees of shift in p50 values as described above.

Results and Discussion Chemical Synthesis

A representative general scheme for synthesizing "PP" compounds is shown in Scheme III (above) and representative compounds PP1, PP2, PP3, PP4, PP5, PP6, PP7, PP8, PP9, PP10, PP11, PP12, PP13, and PP14 are depicted in FIG. 2. All compounds were used for functional and biological in vitro studies. Selected compounds were used for in vivo and structural studies.

Structural Study Showed PP Compounds Bind to the α-Cleft of Hemoglobin

Based on crystallographic binding of vanillin and TD7 to Hb, we structurally modified the TD compounds into PP compounds to increase interactions with Hb, as well as make closer contacts with the F helix. Several PP compounds were crystallized with Hb and with CO-liganded Hb and the crystal structures of several of these complexes in the R2-state conformation were successfully determined. The structure of PP9 which has been refined to 1.9 Å is described here, noting that the other complexes show similar binding, although differences also occur that might explain differences in their functional activities.

Figure 3A:
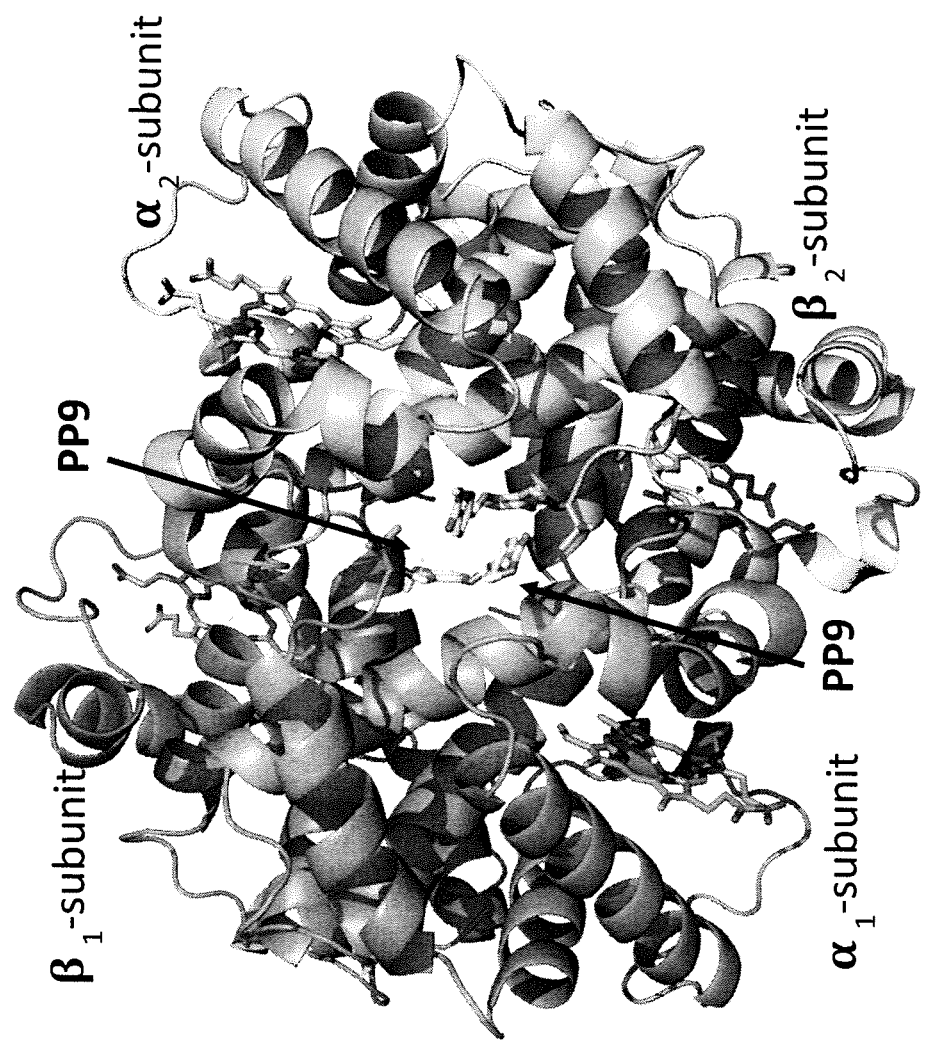
FIGS. 3A and B. A, crystal structure of R2-state Hb in complex with PP9; B, F helix interactions.
Figure 3B:
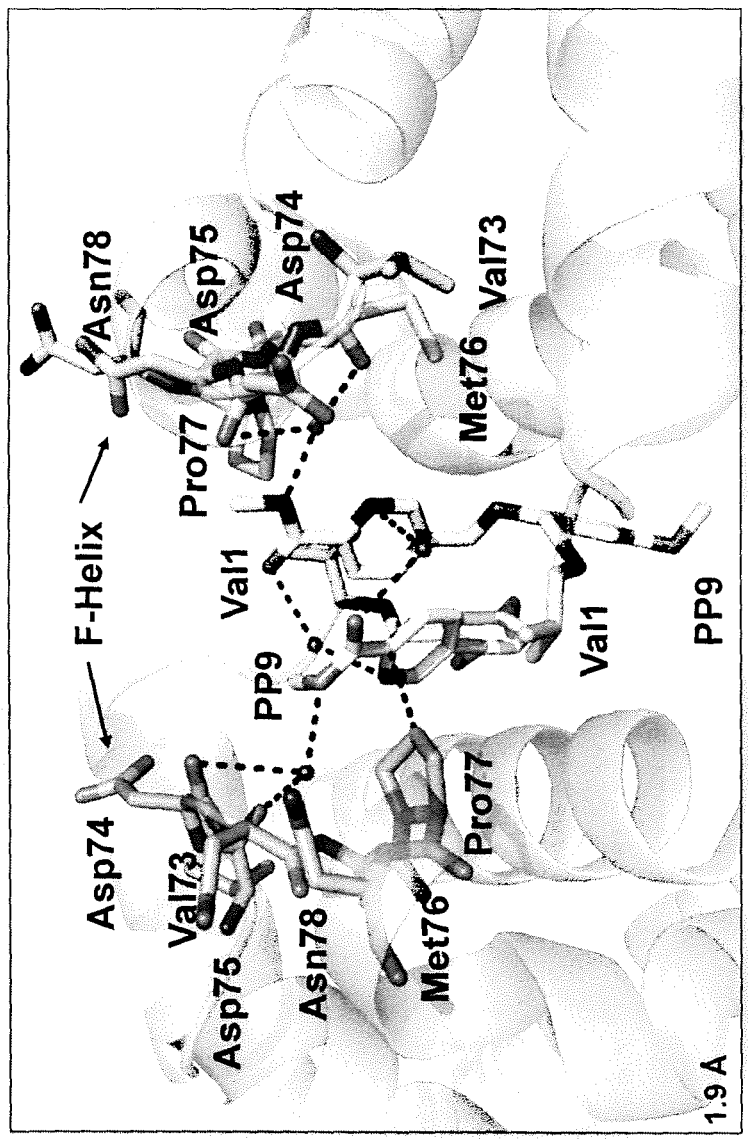

The overall tetrameric structure of PP9 is indistinguishable (rmsd ~0.4 Å) from the native R2 structure (1BBB) or the R2 structure in complex with 5-HMF (PDB code 1QXE) or in complex with TD7. As observed with these compounds, a pair of PP9 covalently bound to the N-terminal αVal1 amines (Schiff-base interaction) in a symmetry-related fashion is seen at the α-cleft as shown in FIG. 3 for PP9. Formation of the Schiff base interaction between the aromatic aldehyde and the αVal1 nitrogen at the α-cleft of Hb directed the ortho-substituted pyridinylmethoxy-methylester upwards towards the surface of the α-cleft and close to the αF helix. Since both molecules bound in a symmetrical fashion, detailed interactions of Hb focus on α2Val1 binding PP9. The benzaldehyde ring makes both intra- and inter-subunit hydrophobic interactions with α2Ala130, α2Ser131, α2Thr134 and α1Thr134. The two pyridine rings from the two PP9 molecules make face-to-face π-π stacking interactions (3.5 Å and greater) with each other. Interestingly, the pyridinylmethoxy-methylester group is oriented toward the αF helix when compared to the hydroxyl moiety of TD7. In fact, the pyridinylmethoxy-methylester makes intra-subunit hydrophobic interactions with α2Pro77 of the αF helix (3.1 Å and greater) compared to the 3.5 Å observed with TD7. In addition, the meta-located pyridine nitrogen and the oxygen of the ester also make extensive and very strong intra-subunit water-mediated interactions with the backbone atoms of α2Val73, α2Asp75 and α2Met76 of the αF helix. These interactions are missing in the TD7 crystal structure. In summary, PP9 binds in a symmetry-related fashion; making several intra- and inter-subunit interactions that leads to stabilization of the R-state Hb, increases the protein affinity for oxygen, and concomitantly reduces hypoxia-induced polymerization. Importantly, the close interactions with the αF helix translate into significant perturbation of the helix and result in polymer destabilization. Finally, the many and intricate interactions with the protein (missing in TD7) stabilize the Schiff-base adduct and reduce dissociation of the bound compound.

In summary, replacing the hydroxyl group with an ester leads to novel compounds that (1) bind strongly to Hb and exhibit increased functional and biological effects; (2) increase strong interactions with the F helix that translate into strong perturbation of the helix and lead to polymer destabilization, leading to a second mechanism of antisickling; and (3) reduce dissociation of the bound compound, thus reducing metabolism. These observations are consistent with functional and biological data.

PP Compounds Increased Hb Affinity for Oxygen in Normal Whole Blood In Vitro

Figure 4:
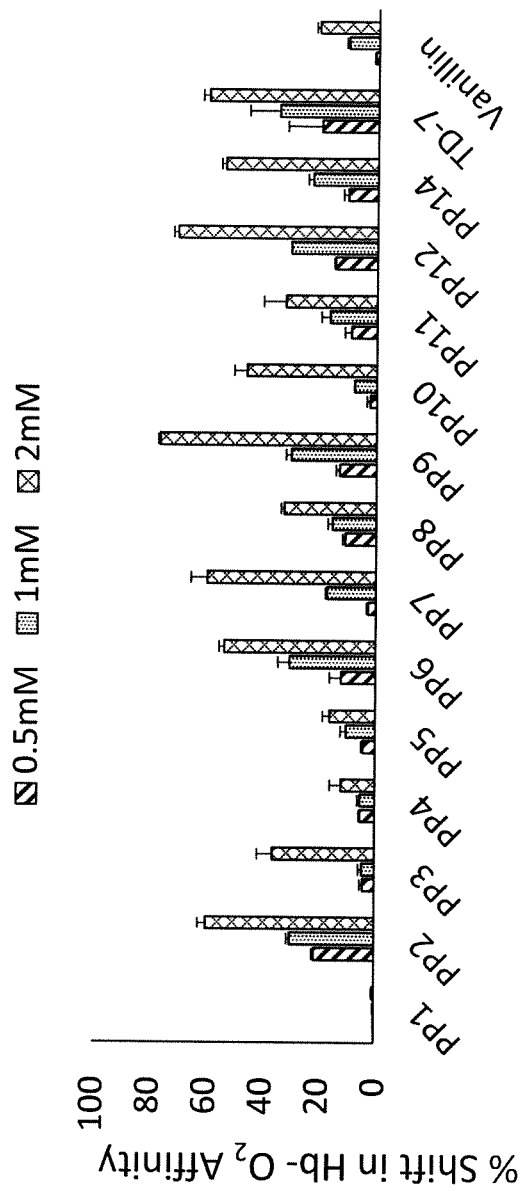
FIG. 4. Dose-dependent in vitro oxygen equilibrium curve (OEC) of PP compounds with normal whole blood.

Aromatic aldehydes are known to prevent hypoxia-induced Hb S polymerization by increasing the Hb affinity for oxygen.[1,2,11,12] We therefore tested the PP compounds in a dose-dependent manner (0.5, 1, 2 mM) for their effect on Hb oxygen binding property. Vanillin and TD7 were tested as controls. The results are summarized in FIG. 4. The study showed a dose dependent effect for all compounds, with PP2, PP6, PP7, PP9, PP12, and PP14 showing the most significant activities. PP1 and PP4 showed minimal effect because of solubility issue. TD7 showed relatively similar potency as most of the best PP compounds although lower than our most potent PP compounds, while vanillin as expected showed very weak functional effect. These findings confirmed that the potent in vitro activity previously seen in TD7 was at least conserved in the novel PP compounds.

PP Compounds Exhibited Extended Functional Effect (Hb Modification) In Vitro

Figure 5A:
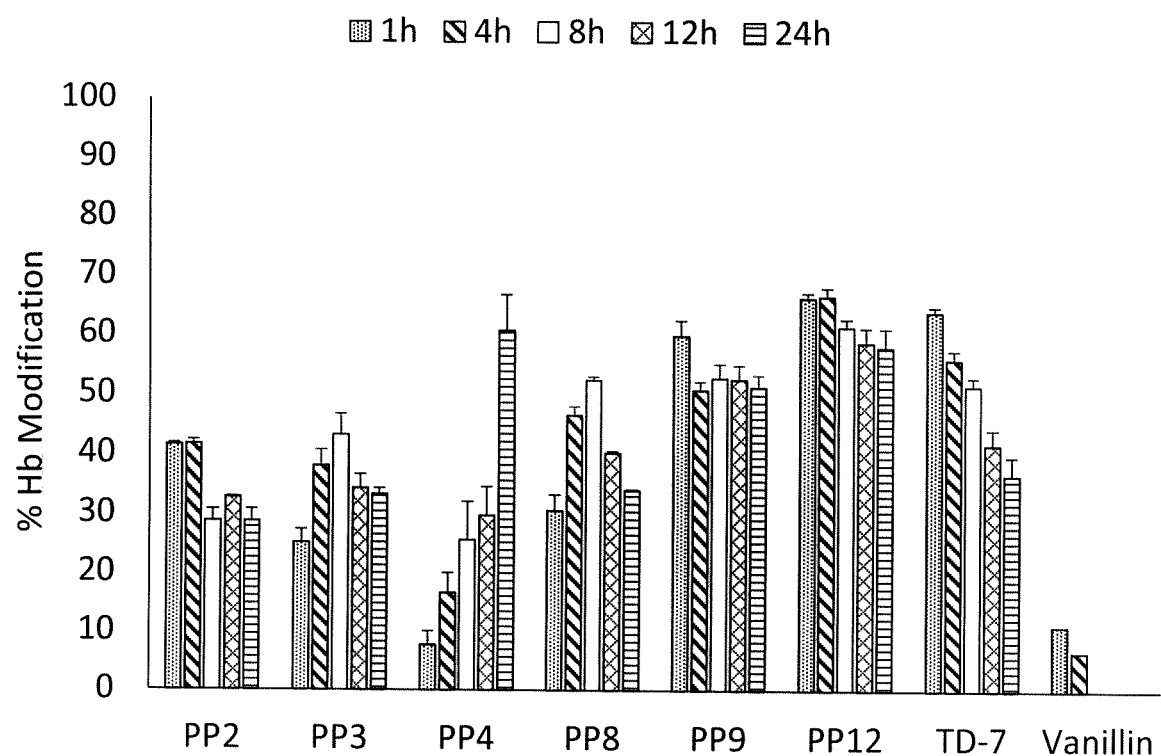
FIGS. 5A and B. Time-dependent in vitro Hb modification by PP compounds with normal whole blood. A, PP compounds 2, 3, 4, 8, 9, and 12; B, PP compounds 6, 10, 7, 11, 14 and 13.
Figure 5B:
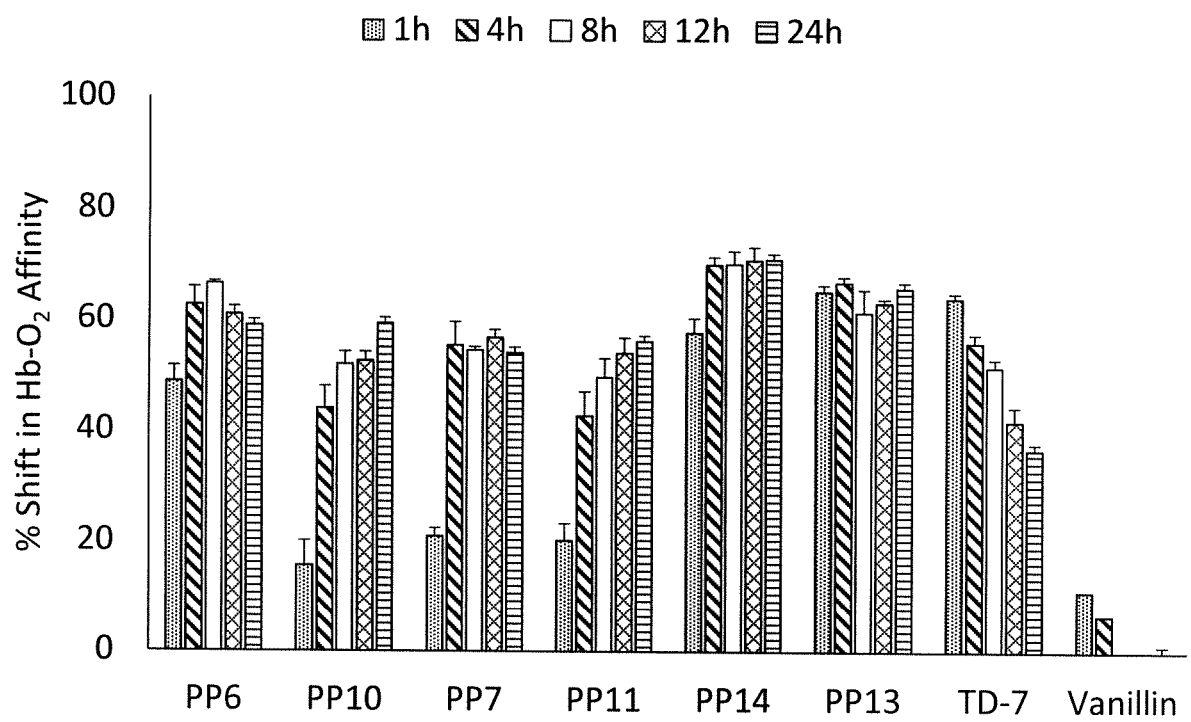

Aromatic aldehydes that increase Hb affinity for oxygen with a concomitant antisickling effect do so by using the aldehyde moiety to bind to the N-terminal αVal1 nitrogens of Hb, forming Schiff-base adducts.[12,11,12] Schiff-base adducts can be accurately quantified by HPLC (Hb modification or Hb adduct). To test the degree and duration of Hb modification, we incubated 2 mM concentrations of PP compounds, and the controls vanillin and TD7 with normal adult blood, hematocrit adjusted to 30% at 37° C. for 24 h. At defined time points (1, 4, 8, 12 and 24 h) aliquot samples were drawn, mixed with a solution containing sodium borohydride/cyanoborohydride to fix the Schiff-base, and subsequently analyzed by cation-exchange HPLC. The results in FIG. 5 showed that Hb modification (adduct formation) was sustained for the entire 24 h experimental period with most of the PP compounds. This observation suggests decreased metabolism of the compounds in whole blood that is partly due to the added structural modifications to the compounds that prevented or reduced enzymatic metabolism, and partly due to strong interactions with the protein to form a more stabilized Schiff-base adduct, thus reducing dissociation of the compound. In contrast, TD7, after reaching a maximum effect at 1 hr, gradually decreased in potency and at 24 hours had lost 45% of its activity, consistent with the low bioavailability of this compound. Also and as expected, vanillin showed no effect after 4 hrs.

As noted above, a Schiff-base interaction is an equilibrium between bound and unbound complex, and when unbound the compound can potentially be metabolized into a pharmacologically inactive non-aldehyde. Therefore, for formation of a stable Schiff-base complex and thus an effective pharmacologic outcome, aromatic aldehydes would make strong interactions to Hb, and exhibit a slow rate of dissociation. Our structural studies clearly show that binding between PP9 and Hb is stronger than binding between TD7 and Hb, suggesting that PP9 dissociates slowly from the bound protein when compared to TD7, and consistent with the results of the time-dependent Hb modification studies. Similar strong interactions with the protein, and particularly with the F helix, are also observed for several of the PP compounds. These findings validate the novelty of these compounds as they clearly suggest an improvement in the metabolic profile of the PP compounds when compared to TD7. As discussed below, these in vitro findings translated into improved PD/PK properties in vivo.

PP Compounds Modified Sickle Hb, Increased its Affinity for Oxygen and Prevented Hypoxia-Induced Erythrocyte Sickling In Vitro.

Figure 6:
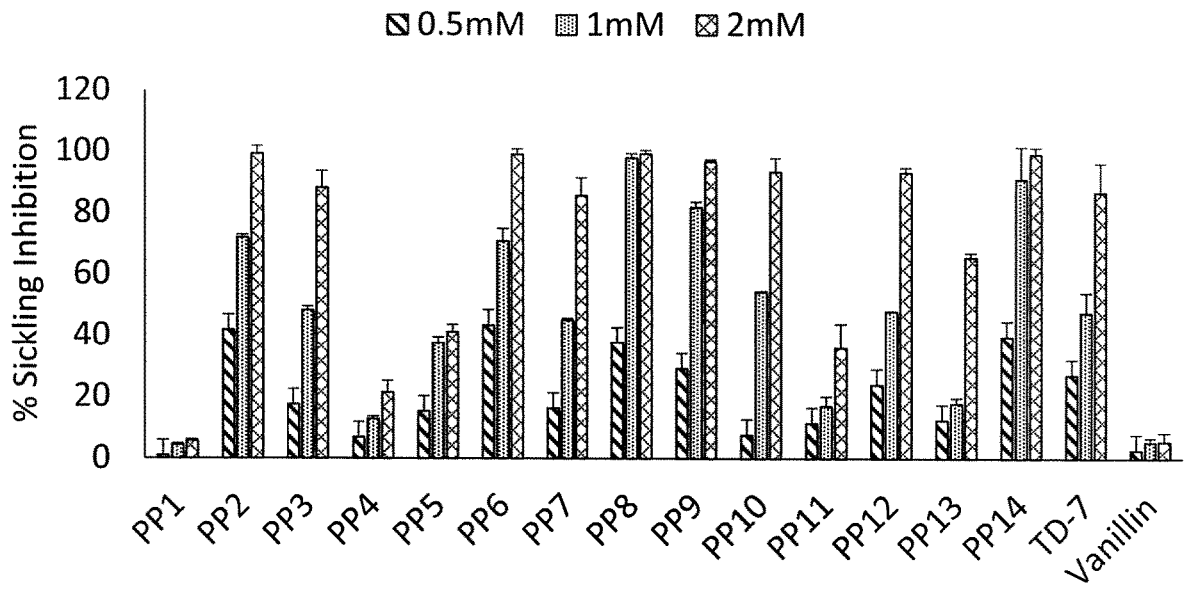
FIG. 6. Dose-dependent in vitro sickling inhibition by PP compounds with sickle red blood cells.
Figure 7:
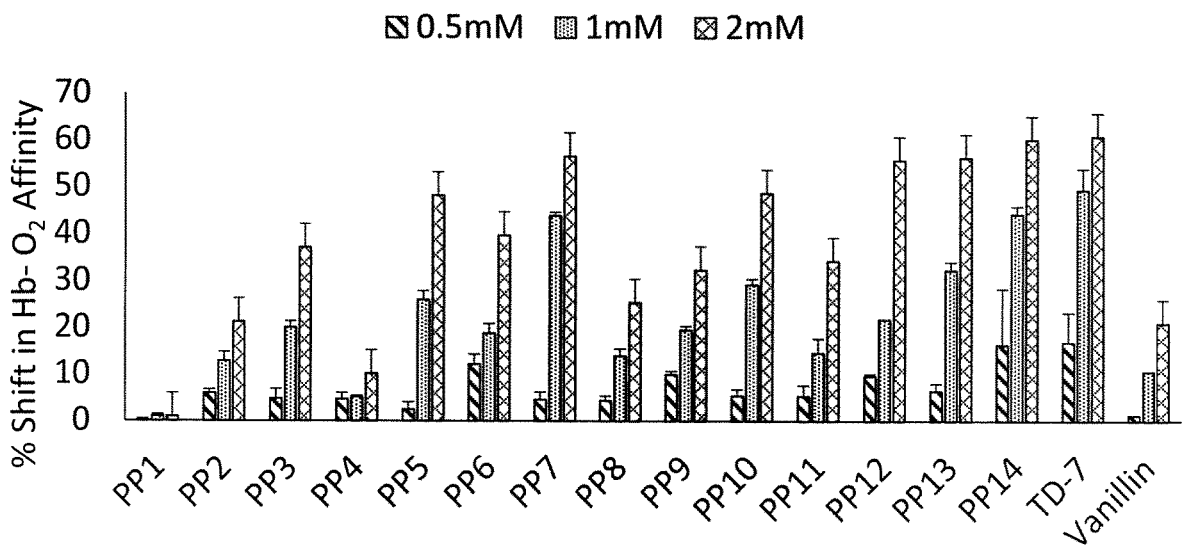
FIG. 7. Dose-dependent in vitro OEC of PP compounds with sickle red blood cells.
Figure 8:
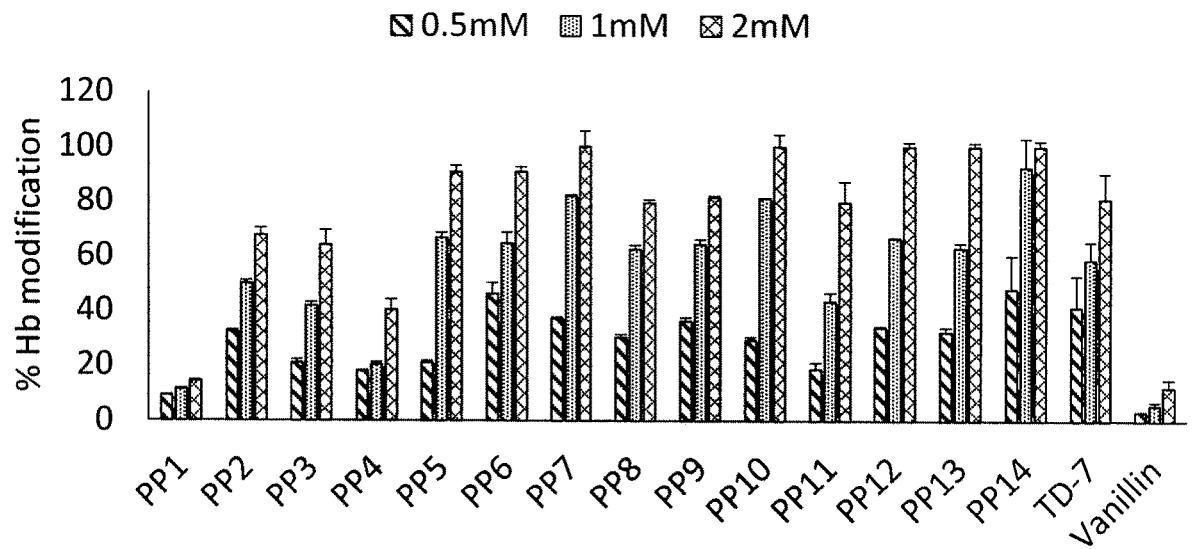
FIG. 8. Dose-dependent in vitro Hb modification by PP compounds with sickle red blood cells.

The studies described above were conducted using normal whole blood. Next, we investigated whether the improvement in Hb oxygen affinity and the compounds sustained activity also translated to similar effects in SS blood from SCD patients. The PP compounds with the control vanillin and TD7 were therefore tested using sickle RBCs for their effect on Hb modification, Hb oxygen affinity and sickling at 0.5, 1 and 2 mM. The results are summarized in FIGS. 6-8. As observed with normal whole blood, the compounds potently increased Hb affinity for oxygen, Hb modification and inhibition of RBC sickling in a dose-dependent fashion. At the lowest concentration of 0.5 mM, four of the compounds, PP2, PP6, PP8, and PP14 showed more than 35% sickling inhibition cinoared to 26% by TD7. At 1 mM, PP8 and PP9 inhibited nearly 100% of sickling, while PP2, PP6, PP14 inhibited sickling by more than 70%. This compares with 47% inhibition by TD7 at 1 mM. Expectedly, vanillin showed only minimal sickling inhibition. It is clear that the modifications of the present compounds has led to significant improvement in antisickling activity. For a disease that requires relatively high concentrations of drug to reach a therapeutic window, a 2-fold increase in potency is very significant, and this fact, taken in conjunction with the fact that the PP compounds show superior PK properties, makes these compounds novel and highly worth developing.

Also noteworthy and significant is the observation that while TD7 and some of the PP compounds demonstrated an almost linear correlation between their ability to increase Hb oxygen affinity and antisickling activity, others, such as PP2, PP3, PP6, PP8, PP9 and PP14 showed a weak correlation between these parameters. In fact, these compounds demonstrated the most potent antisickling effect despite only marginally increasing Hb affinity for oxygen. This observation is consistent with these compounds exhibiting multiple mechanisms of antisickling activity that include increasing the oxygen affinity of Hb, and direct stereospecific polymer destabilization; the latter is validated by the crystal structures that show that PP9 and several of the PP compounds make significant hydrophobic and hydrogen-bond interactions with the F helix. As discussed below, F helix perturbation leads to these compounds inhibiting RBC sickling even at 100% nitrogen, which is independent of the primary antisickling mechanism of increasing Hb oxygen affinity.

PP Compounds Inhibit RBC Sickling Under 100% Nitrogen

Figure 9:
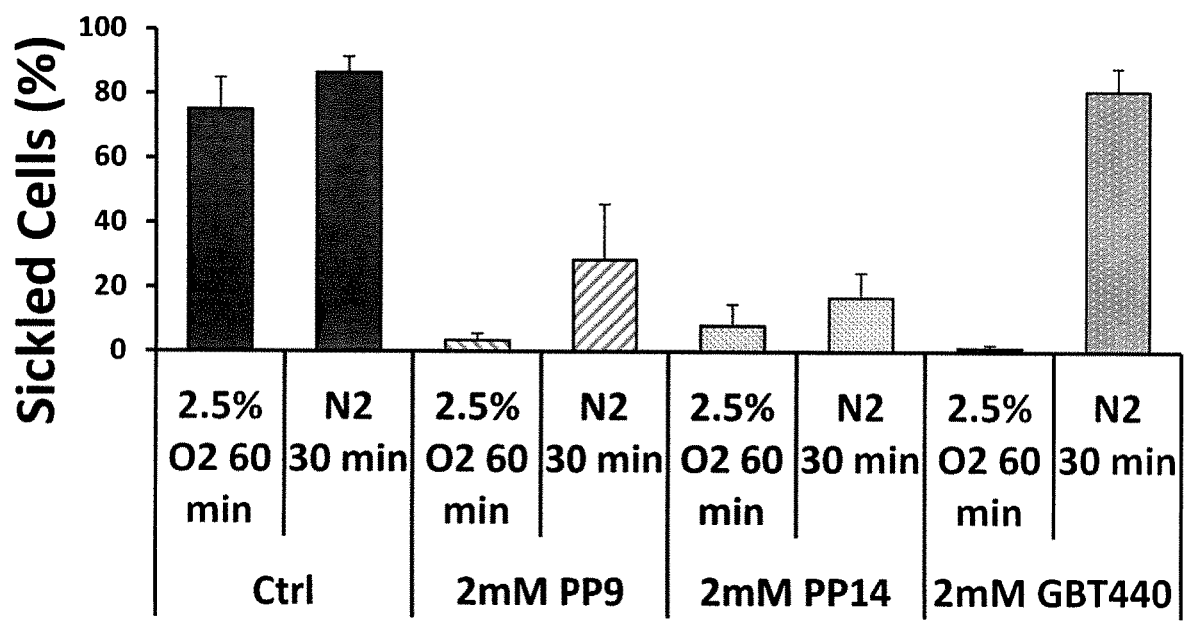
FIG. 9. Antisickling effects of PP compounds and other aromatic aldehydes under 2.5% oxygen gas vs 100% nitrogen gas.

Placing a bulkier group e.g. ester or amide moiety on the pyridine moiety results in compounds that behave differently than previous aromatic antisickling aldehydes. The resulting molecules make closer interactions with the surface located αF helix and lead to stereospecific inhibition of polymer formation. Thus, the compounds exhibit a second antisickling mechanism of action (an Hb-$O_2$ affinity independent antisickling mechanism), and this can be followed by conducting the antisickling assay at 100% nitrogen. Selected PP compounds were therefore tested using sickle RBCs for their antisickling effect at 100% nitrogen. TD7 and GBT440 were used as positive controls. GBT440 is also an antisickling aromatic aldehyde that is currently in phase III clinical studies for the treatment of SCD (clinicaltrials.gov, NCT03036813). GBT440 is highly potent in preventing hypoxia-induced polymerization and concomitant RBC sickling, and has shown proof-of-concept in animal models and humans. As indicated earlier, for internal control purposes, the same samples were used for testing the antisickling effect of these compounds with 2.5% oxygen prior to testing under nitrogen gas, therefore helping elucidate the antisickling effects due to increased Hb affinity for oxygen. The results are summarized in FIG. 9, and clearly showed that at a 2 mM concentration, the compounds not only inhibit sickling via the primary mechanism of action of increasing Hb oxygen affinity, but they also showed a novel mechanism of action by inhibiting sickling under 100% nitrogen, unlike other molecules. The biological data is consistent with the structural data, indicating that these compounds are able to interact very strongly (hydrophobic and hydrogen-bonding) with the surface located αF helix of Hb, leading to destabilization of the polymer with a concomitant antisickling activity that is independent of oxygen affinity for Hb.

PP Compounds Showed Improved Pharmacodynamic Activities In Vivo

Three of the PP compounds (PP6, PP10 and PP14) with high and sustained functional/biological functional/biological activities were selected for an assessment of their in vivo pharmacologic (pharmacodynamic) effects using wild-type C57BL/6 mice. Excipients for formulating the compounds were optimized.

Figure 10A:
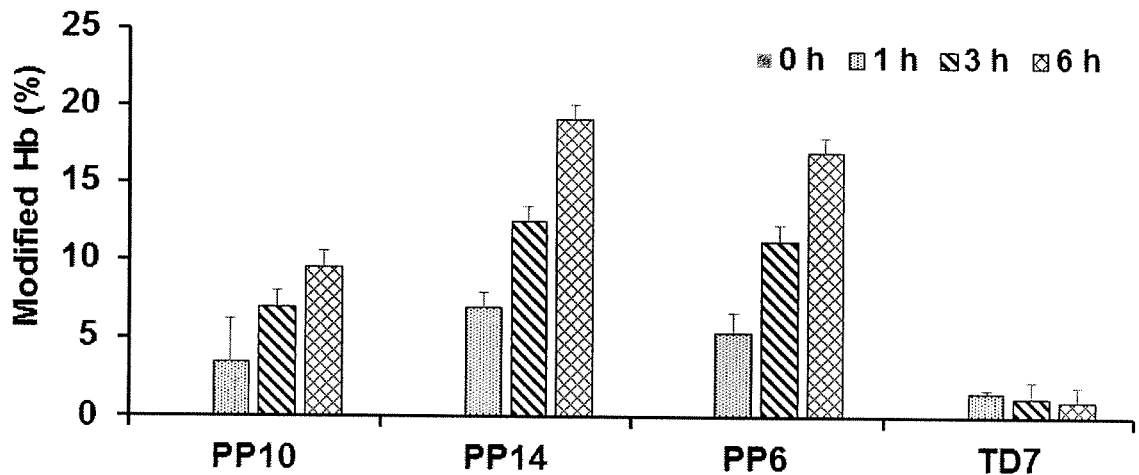
FIGS. 10A and B. In Vivo Pharmacologic effect of PP compounds in wild-type mice. A, time-dependent Hb modification; B, time-dependent Hb oxygen affinity shift.
Figure 10B:
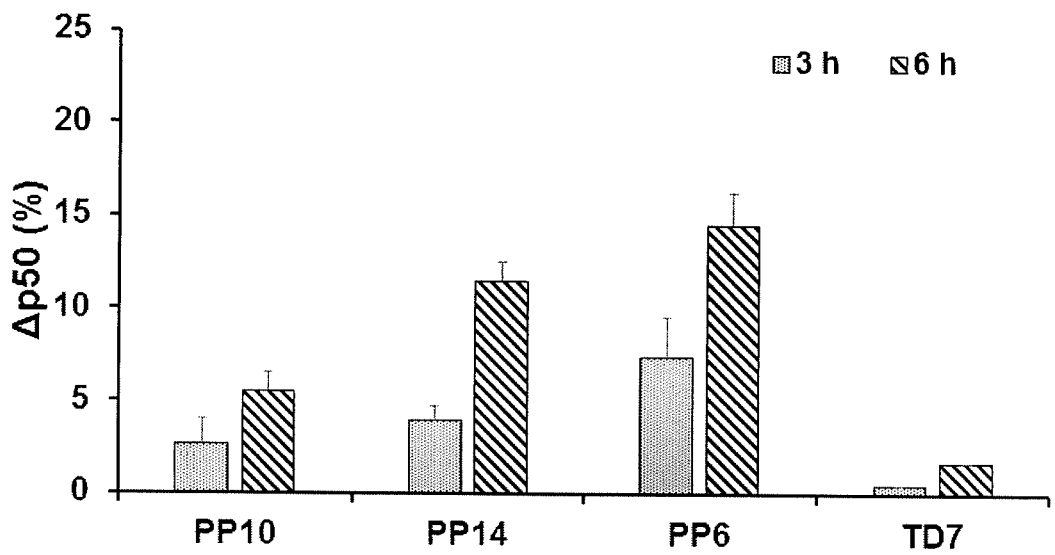

In an earlier experiment, using 30% PEG300 to formulate the test compounds, the animals were treated with a single intraperitoneal (IP) 150 mg/kg body weight) dose of PP6, PP10, PP14. All three selected PP compounds demonstrated significant in vivo modification of intracellular Hb in mice after IP administration, with increasing levels from 1 h to the 6 h experimental period (n=2 mice per compound, FIG. 10A). Mice treated with PP14 demonstrated the highest levels of modified Hb (19.1±0.6% at 6 h), compared to 16.9±1.4% and 9.6±1.9% for PP6-treated and PP10-treated mice, respectively. Conversely, only 1.5±0.3% modified Hb was observed in mice treated with TD7. All three PP compounds led to a significant increase in Hb affinity for oxygen when compared to TD7. Corresponding changes in oxygen affinity (Δp50) were observed at the measured time points of 3 h and 6 h, compared to 0 h pre-treatment samples (FIG. 10B).

Figure 11A:
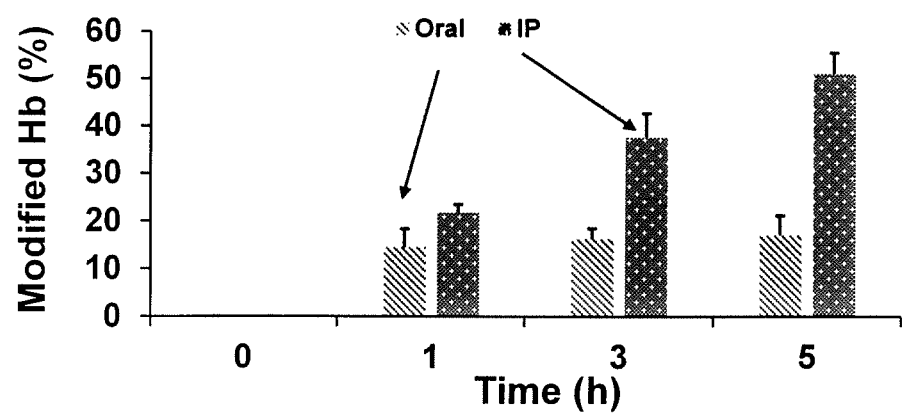
FIGS. 11A and B. In Vivo Pharmacologic effect of PP14 in wild-type mice using optimized vehicle for drug administration. A, time dependent modification of intracellular Hb in wild-type mice after oral (n=3), or IP (n=2) administration of 150 mg/kg PP14; B, time-dependent (5 hrs) Hb oxygen affinity shift in wild-type mice after oral (n=3), or IP (n=2) administration of 150 mg/kg PP14.
Figure 11B:
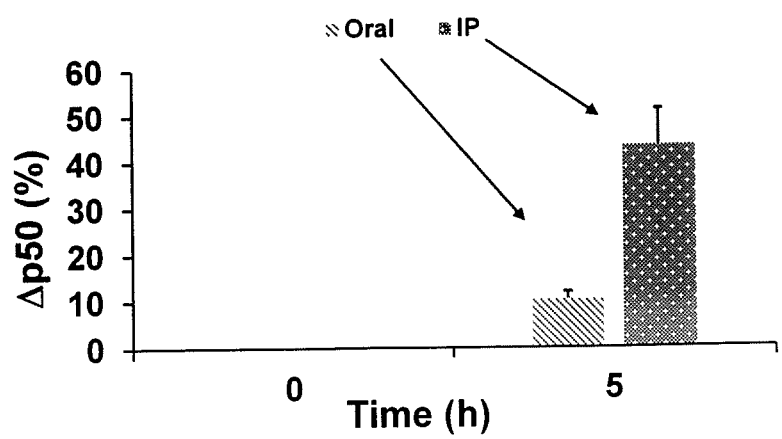

Using the 30% PEG300 excipient did not give a uniform dispersion and this could affect bioavailability and the PD effect. We therefore experimented with several different excipients for formulating one of the compounds, PP14, for testing. The optimal excipient, which gave uniform compound dispersions, was obtained from Catalent Pharma Solutions. Consistent with the optimized formulation, we observed a significant increase in PD effect. At 150 mg/kg, mice treated with PP14 via IP injection showed significantly higher Hb modifications of 21.8*1.6% (1 hr), 37.7*5.0% (3 hr) and 51.1±4.3% (5 hr), respectively (FIG. 11A). This compares to Hb modifications of 7% (1 hr), 13% (3 hr) and 19% (6 hr), respectively by PP14 when 30% PEG300 was used as the excipient (FIG. 10A). The high Hb modification also resulted in significant increases in Hb affinity of 43.5±7.7% at 5 hr (FIG. 11B). This compares to 12% using the excipient 30% PEG300 (FIG. 10B). Clearly optimizing the formulation led to a 3-4 fold more potent compound activity. Using oral gavage with the same excipient also resulted in high levels of modified Hb at 14.5±3.7% (1 hr), 16.3±2.2% (3 hr) and 17.1±4.4% (5 hr), as well as corresponding increase in Hb oxygen affinity of 10.3±1.5% (FIG. 11).

The study demonstrates the superiority of the PP compounds compared to TD7 and vanillin, which is likely attributable to the structural modifications described herein.

CONCLUSION

We have developed new compounds to overcome the disadvantages of predecessor molecules. The compounds exhibit several advantageous attributes: first, the structural modifications allow the compounds to make very strong interactions with the surface located αF helix of Hb, which is known to be important in stabilizing the polymer. The interactions with the F helix destabilize the polymer, resulting in the compounds exhibiting an independent and novel Hb-$O_2$ antisickling mechanism of action, in addition to the primary Hb-$O_2$ dependent antisickling mechanism. This dual mechanism translated into very potent and significantly enhanced antisickling activities. Moreover, the Hb-$O_2$ independent antisickling mechanism permits the prevention of sickling without drastically changing oxygen delivery capabilities, making the compounds more useful in treating SCD compared to other related aromatic aldehydes. This is critical for a disease that is characterized by severe hypoxia. Second, due to the structural modifications, the compounds are resistant to metabolism due to enhanced binding to hemoglobin, which stabilizes the Schiff-base adduct and leads to significantly sustained and improved pharmacologic activities in vitro and in vivo. These attributes are critical properties for a regularly administered agent to treat SCD— as it is chronic condition.

REFERENCES FOR EXAMPLE 1

1. Safo, M. K.; Ahmed, M. H.; Ghatge, M. S.; Boyiri, T. Hemoglobin-ligand binding: Understanding hb function and allostery on atomic level. *Biochim. Biophys. Acta.* 2011, 1814, 797-809.
2. Pauling, L.; Itano, H. A. Sickle cell anemia, a molecular disease. *Science* 1949, 109, 443.
3. Cretegny, I.; Edelstein, S. J. Double strand packing in hemoglobin S fibers, *J. Mol. Biol.* 1993, 230, 733-738.

4. Habara, A.; Steinberg, M. H. Minireview: Genetic basis of heterogeneity and severity in sickle cell disease. *Exp. Biol. Med (Maywood)* 2016, 241, 689-696.

5. Charache, S.; Terrin, M. L.; Moore, R. D.; Dover, G. J.; McMahon, R. P.; Barton, F. B.; Waclawiw, M.; Eckert, S. V. Design of the multicenter study of hydroxyurea in sickle cell anemia. investigators of the multicenter study of hydroxyurea. *Control. Clin. Trials.* 1995, 16, 432-446.

6. Abraham, D. J.; Mehanna, A. S.; Wireko, F. C.; Whitney, J.; Thomas, R. P.; Orringer, E. P. Vanillin, a potential agent for the treatment of sickle cell anemia. *Blood* 1991, 77, 1334-1341.

7. Zaugg, R. H.; Walder, J. A.; Walder, R. Y.; Steele, J. M.; Klotz, I. M. Modification of hemoglobin with analogs of aspirin. *J. Biol. Chem.* 1980, 255, 2816-2821.

8. Abdulmalik, O.; Ghatge, M. S.; Musayev, F. N.; Parikh, A.; Chen, Q.; Yang, J.; Nnamani, I. N.; Danso-Danquah, R.; Eseonu, D. N.; Asakura, K.; Abraham, D. J.; Venitz, J.; Safo, M. K. Crystallographic analysis of human hemoglobin elucidates the structural basis of the potent and dual antisickling activity of pyridyl derivatives of vanillin. *Acta Crystallogr. D Biol. Crystallogr.* 2011, D67, 920-928.

9. Rhoda, M. D.; Martin, J.; Blouquit, Y.; Garel, M. C.; Edelstein, S. J.; Rosa, J. Sickle cell hemoglobin fiber formation strongly inhibited by the Stanleyville II mutation (alpha 78 asn leads to lys), *Biochem. Biophys. Res. Commun.* 1983, 111, 8-13.

10. Safo, M. K.; Abraham, D. J. X-ray crystallography of hemoglobins. *Methods Mol. Med.* 2003, 82, 1-19.

11. Abdulmalik, O.; Safo, M. K.; Chen, Q.; Yang, J.; Brugnara, C.; Ohene-Frempong, K.; Abraham, D. J.; and Asakura, T. 5-hydroxymethyl-2-furfural modifies intracellular sickle haemoglobin and inhibits sickling of red blood cells. *Br. J. Haematol.* 2005, 128, 552-561.

12. Xu, G. G.; Pagare, P. P.; Ghatge, M. S.; Safo, R. P.; Gazi, A.; Chen, Q.; David, T.; Alabbas, A. B.; Musayev, F. N.; Venitz, J.; Zhang, Y.; Safo, M. K.; Abdulmalik, O. Design, Synthesis, and Biological Evaluation of Ester and Ether Derivatives of Antisickling Agent 5-HMF for the Treatment of Sickle Cell Disease. *Mol Pharm.* 2017, 14, 3499-3511.

13. Winn, M. D.; Ballard, C. C.; Cowtan, K. D.; Dodson, E. J.; Emsley, P.; Evans, P. R.; Keegan, R. M.; Krissinel, E. B.; Leslie, A. G. W.; McCoy, A.; McNicholas, S. J.; Murshudov, G. N.; Pannu, N. S.; Potterton, E. A.; Powell, H. R.; Read, R. J.; Vagin, A.; Wilson, K. S. Overview of the CCP4 Suite and Current Developments. *Acta Crystallogr. D Biol. Crystallogr.* 2011, 67 (Pt 4), 235-242.

14. Echols, N.; Grosse-Kunstleve, R. W.; Afonine, P. V.; Bunkóczi, G.; Chen, V. B.; Headd, J. J.; McCoy, A. J.; Moriarty, N. W.; Read, R. J.; Richardson, D. C.; Richardson, J. S.; Terwilliger, T. C.; Adams, P. D. Graphical Tools for Macromolecular Crystallography in PHENIX. *J. Appl. Crystallogr.* 2012, 45 (Pt 3), 581-586.

15. Emsley, P.; Lohkamp, B.; Scott, W. G.; Cowtan, K. Features and Development of Coot. *Acta Crystallogr. D Biol. Crystallogr.* 2010, 66 (Pt 4), 486-501.

16. Brünger, A. T.; Adams, P. D.; Clore, G. M.; DeLano, W. L.; Gros, P.; Grosse-Kunstleve, R. W.; Jiang, J. S.; Kuszewski, J.; Nilges, M.; Pannu, N. S.; Read, R. J.; Rice, L. M.; Simonson, T.; Warren, G. L. Crystallography & NMR System: A New Software Suite for Macromolecular Structure Determination. *Acta Crystallogr. D Biol. Crystallogr.* 1998, 54 (Pt 5), 905-921.

EXAMPLE 2

General Procedure to Prepare the Thiozolidinemodified Compounds

To a stirring solution of L-cysteine ethyl ester hydrochloride (15.9 mmol) and ethyl-diisopropyl amine (15.9 mmol) in anhydrous ethanol (30 mL) at room temperature is added dropwise an equimolar amount of the aldehyde compound (15.9 mM) in anhydrous ethanol (20 mL). The reaction mixture is stirred at the same temperature for 2 hrs or overnight. The mixture is then diluted with water (100 mL) and the product extracted with ethyl acetate (3×50 mL). The organic phase is dried, evaporated, and the product purified through a column with EtOAc: Hexanes as the eluent.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A vanillin-derived compound having Formula I:

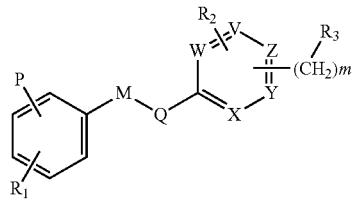

where
R1 is a H or hydroxy, with the caveat that R1 is H at at least three locations on the benzene ring;
R2 is H or a heterocycle with the caveat that R2 is H at at least three locations selected from W, V, Z, Y, and X;
R3 is alkyl ester;
M is O;
Q is $CH_2$;
X, Y, Z, W and V are the same or different and are independently CH or N with the caveat that only one of X, Y, Z, W, and V is N;
m=0-6, and
P=CHO or a promoiety of CHO, wherein P is only at one location on the benzene ring;
wherein R1 is hydroxy at a carbon meta to the carbon linked to the oxygen of the ether linkage and wherein P is at a carbon ortho to the carbon linked to the oxygen of the ether linkage;
or a pharmaceutically acceptable salt thereof.

2. The vanillin-derived compound of claim 1, wherein the vanillin-derived compound is designed to bind to the F helix of hemoglobin (Hb).

3. The vanillin-derived compound of claim 1 wherein P is CHO.

4. The vanillin-derived compound of claim 1 where P is a promoiety.

5. The vanillin-derived compound of claim 4, wherein the promoiety is

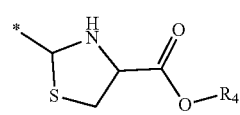

where R4 is H or a linear or branched C1-C5 alkyl; and where the bond marked with * bonds directly to a carbon of the benzene ring.

6. The vanillin-derived compound of claim 1, wherein the vanillin-derived compound is

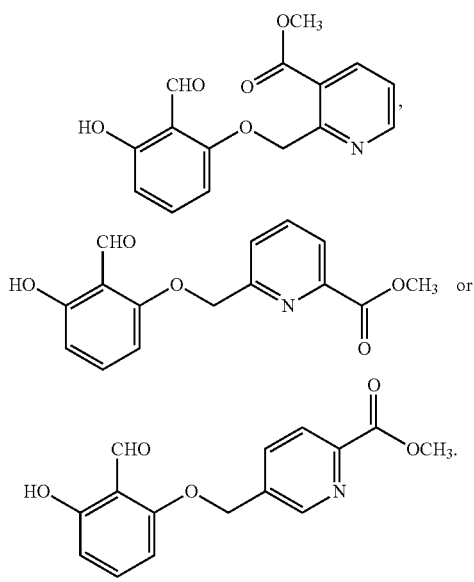

7. The vanillin-derived compound of claim 6, wherein the vanillin-derived compound is

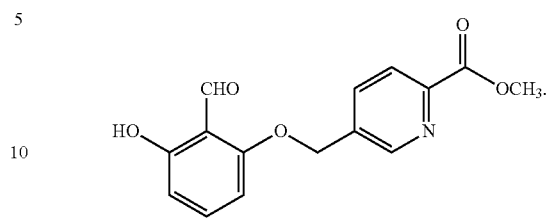

8. The vanillin derived compound of claim 1, wherein the pharmaceutically acceptable salt is an HCl salt.

9. A composition comprising,
at least one vanillin-derived compound of claim 1.

10. The composition of claim 9, which is in a form for oral administration.

* * * * *